(12) United States Patent
Suzuki et al.

(10) Patent No.: US 7,612,115 B2
(45) Date of Patent: Nov. 3, 2009

(54) AQUEOUS PHARMACEUTICAL COMPOSITIONS

(75) Inventors: Hidekazu Suzuki, Tokyo (JP); Takahiro Wada, Tokyo (JP); Masanobu Kirita, Chiba (JP); Masanobu Takeuchi, Tokyo (JP)

(73) Assignee: Wakamoto Pharmaceutical Co., Ltd., Tokyo (JP)

( * ) Notice: Subject to any disclaimer, the term of this patent is extended or adjusted under 35 U.S.C. 154(b) by 206 days.

(21) Appl. No.: 11/374,450

(22) Filed: Mar. 13, 2006

(65) Prior Publication Data

US 2006/0172969 A1    Aug. 3, 2006

Related U.S. Application Data

(63) Continuation of application No. 10/344,189, filed on Jun. 2, 2003, now abandoned.

(30) Foreign Application Priority Data

Aug. 8, 2000    (JP) ............................. 2000-240455

(51) Int. Cl.
*A61K 47/00*    (2006.01)
*A61K 31/715*   (2006.01)
*A61K 31/47*    (2006.01)

(52) U.S. Cl. ...................... 514/772.2; 514/58; 514/311; 514/312

(58) Field of Classification Search ............... 514/772.2, 514/311, 312, 58
See application file for complete search history.

(56) References Cited

U.S. PATENT DOCUMENTS

| 5,164,194 | A | | 11/1992 | Hettche | |
| 5,624,962 | A | | 4/1997 | Takeuchi et al. | |
| 5,756,552 | A | * | 5/1998 | Takeuchi et al. | 514/772.2 |
| 5,929,115 | A | * | 7/1999 | Takeuchi et al. | 514/567 |
| 6,132,751 | A | * | 10/2000 | Suzuki et al. | 424/422 |
| 6,432,439 | B1 | * | 8/2002 | Suzuki et al. | 424/427 |
| 6,495,603 | B1 | * | 12/2002 | Miyake et al. | 514/601 |
| 7,105,512 | B2 | * | 9/2006 | Morizono et al. | 514/226.5 |

FOREIGN PATENT DOCUMENTS

| EP | 0 694 310 A1 | 1/1996 |
| EP | 0 782 850 A1 | 7/1997 |
| EP | 0 950 419 A1 | 10/1999 |
| JP | 1-153639 | 6/1989 |
| JP | 2001-48807 | 2/2001 |
| WO | WO 94/23750 | 10/1994 |
| WO | WO 98/30221 | 7/1998 |
| WO | WO 9963968 A1 * | 12/1999 |

OTHER PUBLICATIONS

Enclosed copy of abstract for WO 9963968 A1 (1999).*

* cited by examiner

*Primary Examiner*—Kevin Weddington
(74) *Attorney, Agent, or Firm*—Chapman and Cutler LLP

(57) ABSTRACT

The present invention has an object to provide an antibacterial aqueous pharmaceutical composition and an aqueous pharmaceutical composition which have a sufficiently low gelation temperature even when new quinolone antibacterial agents such as ofloxacin as the active ingredient and can be retained at the administration site for a long time by virtue of rapid viscosity increase after administration in spite of their being liquid at administration and thereby attain high availability of pharmaceutical agent.

The present invention relates to an antibacterial aqueous pharmaceutical composition
which comprises: 2.8 to 4 w/v % of methylcellulose, the 2 w/v % aqueous solution of which has a viscosity of 12 mPa·s or below at 20° C.; 1.5 to 2.3 w/v % of citric acid; 2 to 4 w/v % of polyethylene glycol; and 0.1 to 0.5 w/v % of ofloxacin.

5 Claims, 2 Drawing Sheets

AQUEOUS PHARMACEUTICAL COMPOSITIONS

TECHNICAL FIELD

The present invention relates to an antibacterial aqueous pharmaceutical composition and an aqueous pharmaceutical composition which have a sufficiently low gelation temperature even when new quinolone antibacterial agents such as ofloxacin as the active ingredient and can be retained at the administration site for a long time by virtue of rapid gelation rate which leads to rapid viscosity increase after administration in spite of their being liquid at administration, and thereby attain high availability of pharmaceutical agent.

BACKGROUND ART

Since a majority of a pharmaceutical agent is flown from eyes to nose when the pharmaceutical agent is administered to eyes, study to stay a pharmaceutical agent on the surfaces of eyes as long time as possible by increasing the viscosity of a preparation has been progressed. In order to increase the viscosity of a preparation, a polymer compound is generally added. However, when the viscosity of a preparation is increased, there arises dispersion in an administration amount, and such a defect is caused that administration of a constant amount becomes difficult.

The viscosity of an aqueous solution of a polymer compound is generally lowered when a temperature is arisen. However, an aqueous solution of methylcellulose (MC), hydroxypropylmethylcellulose, poly(vinyl alcohol) or the like has the characteristic that it is gelled and the viscosity is increased at a certain temperature or a higher temperature.

In Japanese Patent No. 2729859, a gelation temperature was successfully lowered to a temperature around a body temperature of human (40° C. or less) by adding 1.2 to 2.3 w/v % of citric acid and further 0.5 to 13 w/v % of polyethylene glycol (PEG) into 0.2 to 2.1 w/v % of methylcellulose, the 2 w/v % aqueous solution of which has a viscosity 13 to 12000 mPa·s at 20° C. Since this preparation has the characteristics that the preparation is liquid before administration, so that is easy to be administered. In addition the preparation is gelled by a body temperature after administration to increase the viscosity, so that the preparation has the advantages that retention effect of a pharmaceutical agent at the administration site is improved and the bioavailability (BA) of a pharmaceutical agent is improved.

The present inventor tried to apply a thermally gelling preparation described in Japanese Patent No. 2729859 to new quinolone antibacterial agents including ofloxacin which is a synthetic antibacterial agent. However, when an ophthalmic solution of ofloxacin prepared according to the thermally gelling composition described in Japanese Patent No. 2729859 and a commercially available aqueous ofloxacin ophthalmic solution were compared, there was no difference in intraocular dynamic of ofloxacin between both ophthalmic solutions.

SUMMARY OF THE INVENTION

An object of the present invention is to provide an antibacterial aqueous pharmaceutical composition and an aqueous pharmaceutical composition which have a sufficiently low gelation temperature even when new quinolone antibacterial agents such as ofloxacin as the active ingredient and can be retained at the administration site for a long time by virtue of rapid gelation rate which leads to rapid viscosity increase after administration in spite of their being liquid at administration, and thereby attain high availability of pharmaceutical agent.

The present invention provides an antibacterial aqueous pharmaceutical composition
which comprises: 2.8 to 4 w/v % of methylcellulose, the 2 w/v % aqueous solution of which has a viscosity of 12 mPa·s or below at 20° C.; 1.5 to 2.3 w/v % of citric acid; 2 to 4 w/v % of polyethylene glycol; and 0.1 to 0.5 w/v % of ofloxacin.

The antibacterial agent comprised in the antibacterial aqueous pharmaceutical composition of the present invention is not limited to ofloxacin, but other new quinolone antibacterial agents such as levofloxacin and moxifloxacin hydrochloride may be also used.

The present invention also provides an aqueous pharmaceutical composition
which comprises: 2.3 to 8 w/v % of methylcellulose, the 2 w/v % aqueous solution of which has a viscosity of 12 mPa·s or below at 20° C.; 0.14 to 4 w/v % of multivalent carboxylic acid or lactic acid; and/or 0.5 to 13 w/v % of polyethylene glycol, as well as an effective amount of a pharmaceutical agent.

DETAILED DISCLOSURE OF THE INVENTION

Figure 1:
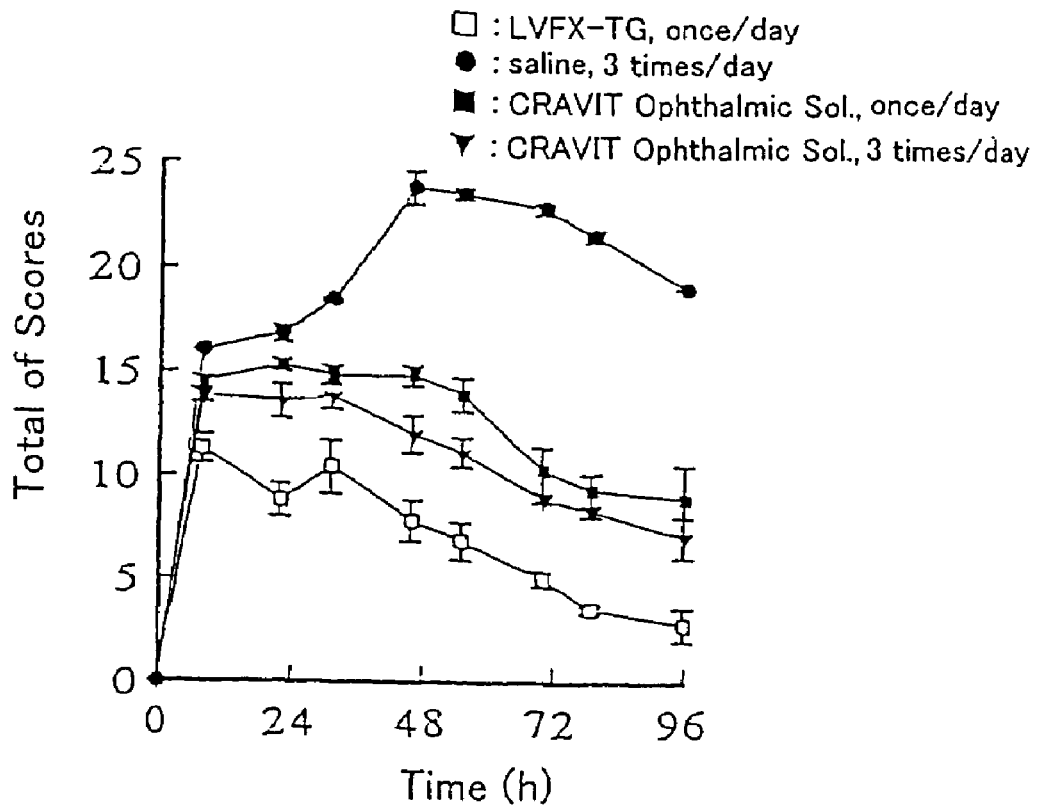
FIG. 1 is a graph showing the test results of Test Example 15 herein.

The present invention will be described in detail below.

The antibacterial aqueous pharmaceutical composition of the present invention is a gelable preparation containing ofloxacin as an active ingredient. The antibacterial aqueous pharmaceutical composition of the present invention contains 2.8 to 4 w/v % of methylcellulose, the 2 w/v % aqueous solution of which has a viscosity of 12 mPa·s or below at 20° C., 1.5 to 2.3 w/v % of citric acid, and 2 to 4 w/v % of polyethylene glycol.

In Japanese Patent No. 2729859, a gelation temperature was successfully lowered to a temperature around a body temperature of human (40° C. or below) by adding 1.2 to 2.3 w/v % of citric acid and further 0.5 to 13 w/v % of polyethylene glycol (PEG) into 0.2 to 2.1 w/v % of methylcellulose the 2 w/v % aqueous solution of which has a viscosity of 13 to 12000 mPa·s or below at 20° C. However, when new quinolones antibacterial agents including ofloxacin are used as an active ingredient, the sufficient efficacy could not be exerted.

The present inventor intensively studied and, as a result, found that an aqueous pharmaceutical composition in which administration amount has no dispersion because the composition is liquid form at administration, and which attains high availability of an active ingredient by virtue of its low gelation temperature and high gelation rate, can be obtained by using methylcellulose, the 2 w/v % aqueous solution of which has the viscosity of 12 mPa·s or below at 20° C. of and incorporating citric acid and polyethyleneglycol thereinto at a specific ratio. The viscosity of a 2 w/v % aqueous solution of methylcellulose at 20° C. used in the present invention is preferably 3 to 5 mPa·s.

The antibacterial aqueous pharmaceutical composition of the present invention contains 2.8 to 4 w/v % of methylcellulose, the 2 w/v % aqueous solution of which has the viscosity of 12 mPa·s or below at 20° C. When the content is less than 2.8 w/v %, a gelation temperature may not be sufficiently lowered, and a rise in the viscosity due to a body temperature may also be insufficient. When the content exceeds 4 w/v %, the viscosity may become high, and administration of a constant amount may become difficult. Additionally, when it is used as an ophthalmic solution, the feeling at administration is inferior depending on administration places, such that the ophthalmic solution is attached to the surrounding of eyes, and thus unpleasant sticky feeling is produced and, furthermore, large scale preparation may become difficult. Now, the content of a methoxyl group of methylcellulose used in the present invention is preferably 26 to 33%.

The antibacterial aqueous pharmaceutical composition of the present invention comprises 1.5 to 2.3 w/v % of citric acid. When the content is less than 1.5 w/v %, a gelation temperature is not sufficiently lowered. On the contrary, when the content exceeds 2.3 w/v %, the stimulation may become too strong when the composition is administered to eyes; thus it is not preferable. Citric acid may be incorporated in the form of a salt thereof. An amount to be incorporated in that case is determined in terms of an acid.

The antibacterial pharmaceutical composition of the present invention comprises 2 to 4 w/v % of polyethylene glycol. When the content is less than 2 w/v %, a gelation temperature may be not sufficiently lowered. When the content exceeds 4 w/v %, the viscosity may become high, administration of a constant amount may become difficult and, for example, when the composition is used as an ophthalmic solution, the feeling at administration may be inferior depending on administration places, such that the ophthalmic solution is attached to the surrounding of eyes, and thus the unpleasant sticky feeling is caused.

Polyethylene glycol used in the present invention is not particularly limited, but commercially available ones can be appropriately used. Examples thereof include, among others, PEG-200, -300, -600, -1,000, -1,540, -2,000, -4,000, -6,000, -20,000, -50,000, -500,000, -2,000,000 and -4,000,000 (the foregoing are manufactured by Wako Pure Chemical Industries, Ltd.); Macrogol-200, -300, -400, -600, -1,500, -1,540, -4,000, -6,000 and -20,000 (foregoing are manufactured by NOF Corporation).

A weight average molecular weight of polyethylene glycol used in the present invention is preferably 300 to 50,000. When the weight is less than 300, an osmotic pressure may become high and, in particular, in the case of an ophthalmic solution, the stimulation at administration may become strong; thus it is not preferable. On the other hand, when the weight exceeds 50,000, the viscosity at the liquid state may be high and, for example, when used as an ophthalmic solution, this leads to deterioration of the feeling at administration such that the composition is attached to surrounding of eyes to cause the unpleasant sticky feeling; thus it is not preferable. More preferably, the weight is 400 to 20,000. In addition, two or more polyethylene glycols may be mixed to adjust a weight average molecular weight to the aforementioned preferable range.

The antibacterial aqueous pharmaceutical composition of the present invention comprises ofloxacin at an amount of 0.1 to 0.5 w/v % as an active ingredient. When the amount is less than 0.1 w/v %, the sufficient efficacy of pharmaceutical agent may not be exerted and, when the amount exceeds 0.5 w/v %, the stability of a preparation may be problematic.

The antibacterial aqueous pharmaceutical composition of the present invention contains ofloxacin as an active ingredient, and levofloxacin and moxifloxacin hydrochloride which are the same new quinolone antibacterial agent, may be also used as an active ingredient.

The antibacterial aqueous pharmaceutical composition of the present invention having the aforementioned constitution has the characteristics that a gelation temperature is low, the viscosity reaches the sufficient viscosity at a low temperature and a gelling rate is high. When the antibacterial aqueous pharmaceutical composition of the present invention is used, for example, as an ophthalmic solution, since it is retained on the surface of eyes for a long time, such the effects are exerted that the transferring property of a pharmaceutical agent into eye tissue is also excellent, and the availability of pharmaceutical agent is high.

The present invention was made in view of that there was no conventionally known gelled preparation containing new quinolone antibacterial agents such as ofloxacin as an active ingredient, in which there is no dispersion in an administration amount because of sufficiently low viscosity at administration, a gelation temperature is sufficiently low, and the availability of pharmaceutical agent is excellent. The present inventor further studied, and found that the similar excellent properties can be exerted also when other pharmaceutical agents as an active ingredient are applied to such the pharmaceutical composition. An aqueous pharmaceutical composition containing other pharmaceutical agents as an active ingredient like this is also one aspect of the present inventions.

When other pharmaceutical agents are used as an active ingredient, unlike the case where new quinolone antibacterial agents such as ofloxacin are contained as an active ingredient, it is necessary to appropriately change the composition of the aqueous pharmaceutical composition in conformity with a pharmaceutical agent to be used. In addition, citric acid is used in the antibacterial aqueous pharmaceutical composition containing new quinolone antibacterial agents such as ofloxacin as an active ingredient, but it was found that other multivalent carboxylic acids, lactic acid or gluconic acid may be used in place of citric acid. Furthermore, it was made clear that the similar effects are exerted by use of either one of multivalent carboxylic acid, lactic acid or gluconic acid and polyethylene glycol without combined use of them, depending on a pharmaceutical agent to be used as an active ingredient.

An amount of said methylcellulose in the aqueous pharmaceutical composition of the present invention to be incorporated may be appropriately set within a range of 2.3 to 8 w/v % depending on a pharmaceutical agent to be used. When the amount is less than 2.3 w/v %, a gelation temperature may not be sufficiently lowered, and a rise in the viscosity due to a body temperature may be also insufficient. When the amount exceeds 8 w/v %, the viscosity may become too high, administration of a constant amount may become difficult and, for example, when used as an ophthalmic solution, the feeling at administration is inferior depending on administration places, such that the composition is attached to the surrounding of eyes and the unpleasant sticky feeling is caused and, furthermore, large scale preparation may become difficult.

An amount of multivalent carboxylic acid, lactic acid or gluconic acid in the aqueous pharmaceutical composition of the present invention to be incorporated may be appropriately set within a range of 0.14 to 4 w/v % depending on a pharmaceutical agent to be used. When the amount is less than 0.14 w/v %, a gelation temperature may not be sufficiently lowered and, when the amount exceeds 4 w/v %, the stimulation may become too strong when the composition is administered to eyes; thus it is not preferable.

Examples of the multivalent carboxylic acid which can be used in the present invention include aspartic acid, glutamic acid, gluconic acid, citric acid, tartaric acid, malic acid, fumaric acid, succinic acid, maleic acid and the like. In addition, multivalent carboxylic acid may be incorporated in the form of a salt or a hydrate thereof. An amount to be incorporated in that case is determined in terms of anhydrous acid.

An amount of polyethylene glycol in the aqueous pharmaceutical composition of the present invention to be incorporated is 0.5 to 13 w/v %. When the amount is less than 0.5 w/v %, a gelation temperature is not sufficiently lowered and, when the amount exceeds 13 w/v %, the viscosity may become too high, administration at a constant amount may become difficult and, for example, when the composition is used as an ophthalmic solution, the feeling at administration is inferior depending on administration places, such that the composition is attached to the surrounding of eyes and the unpleasant sticky feeling is caused and, further, large-scale preparation may become difficult. When the amount is within a range of 0.5 to 13 w/v %, the amount can be appropriately set according to a pharmaceutical agent to be used.

In the aqueous pharmaceutical composition of the present invention, a sufficiently low gelation temperature may be realized by using multivalent carboxylic acid, lactic acid or gluconic acid with polyethylene glycol combinedly. However, as described above, depending on a pharmaceutical agent to be contained, either one of multivalent carboxylic acid, lactic acid or gluconic acid and polyethylene glycol may be contained without combined use of them.

For example, when a gelled preparation is prepared by using tranilast, which is an anti-allergic agent, as an active ingredient, it is not preferable to add multivalent carboxylic acid such as citric acid, since tranilast forms an insoluble complex with multivalent carboxylic acid such as citric acid. However, by using methylcellulose, the 2 w/v % aqueous solution of which has a viscosity of 12 mPa·s or below at 20° C., it was made clear that, when a pharmaceutical agent such as tranilast is used as an active ingredient, a gelation temperature can be sufficiently lowered by using the aforementioned methylcellulose and polyethylene glycol at a prescribed amount without using multivalent carboxylic acid or lactic acid.

The pharmaceutical agent used in the aqueous pharmaceutical composition of the present invention is not particularly limited, but includes chemotherapeutics such as amphotericin B, miconazole nitrate and idoxuridine; antibiotics such as chloramphenicol, colistin sodium methanesulfonate, carbenicillin disodium and gentamicin sulfate; anti-allergic agents such as acitazanolast, ketotifen fumarate, disodium cromoglicate and tranilast; anti-inflammatories such as betamethasone sodium phosphate, dexamethasone, fluoromethorlone, dipotassium glycyrrhizinate, lysozyme chloride, diclofenac sodium, pranoprofen, indometacin, cortisone acetate, azulene, allantoin, 6-aminocaproic acid, predonisolone acetate and bromfenac sodium; miotics such as pilocarpine hydrochloride and carbachol; vitamins such as flavin adenine dinucleotide, pyridoxal phosphate and cyanocobalamin; vasoconstrictors such as naphazoline nitrate and phenylephrine hydrochloride; anti-histamines such as chlorpheniramine maleate and diphenhydramine hydrochloride; mydriatics such as tropicamide and phenylephrine hydrochloride; glaucoma treating agents such as timolol maleate, carteolol hydrochloride, betaxolol hydrochloride, isopropylunoproston, nipradirol, latanoprost, dorzolamide, levobunolol hydrochloride and pilocarpine hydrochloride; cataract treating agents such as glutathioneandpyrenoxine; local anesthetics such as lidocaine hydrochloride and oxybuprocaine hydrochloride; ophthalmic diagnostic agents such as sodium fluorescein; immunosuppressors such as cyclosporin, azathioprine, taclolimus and mycophenolic acid; metabolic antagonists such as fluorouracil and tegafur; decongestants such as epinephrine hydrochloride; diabetic retinopathy treating agents such as [5-(3-thienyl)tetrazol-1-yl]acetic acid and aminoguanidine; amino acids such as sodium chondroitin sulfate and aminoethanesulfonic acid; autonomics such as neostigmine methylsulfate; anti-dermoinfectives such as bifonazole, siccanin, bisdecalinium acetate, clotrimazole and salicylic acid; dermatics for purulence such as sodium sulfamethoxazole, erythromycin and gentamicin sulfate; anti-inflammatory and analgesic agents such as indometacin, ketoprofen, betamethasone valerate and fluocinolone acetonide; anti-itchings such as diphenhydramin; local anesthetics such as procaine hydrochloride and lidocaine hydrochloride; antibiotics for dermatologic use such as iodine, povidone iodine, benzalkonium chloride and chlorhexidine gluconate; anti-histamines such as diphenhydramine hydrochloride and chlorpheniramine maleate; agents for genital organs such as clotrimazole, naphazoline nitrate, ketotifen fumarate and miconazole nitrate; agents for otic and nasal use such as tetryzoline hydrochloride; bronchodilators such as aminophylline; metabolic antagonists such as fluorouracil; hypnotic sedatives such as diazepam; antipyretic analgesic and anti-inflammatory agents such as aspirin, indometacin, sulindac, phenylbutazone and ibuprofen; adrenal hormone preparations such as dexamethasone, triamcinolone and hydrocortisone; local anesthetics such as lidocaine hydrochloride; dermatics for purulence such as sulfisoxazole, kanamycin, tobramycin and erythromycin; synthetic antibacterial agents such as enoxacin, ciprofloxacin hydrochloride, lomefloxacin hydrochloride, ofloxacin, cinoxacin, sparfloxacin, tosfloxacin tosilate, nalidixic acid, norfloxacin, freroxacin, grepafloxacin hydrochloride, gatifloxacin, prulilfloxacin, sitafloxacin, pazufloxacin tosilate, gemifloxacin, moxifloxacin hydrochloride, olamufloxacin and levofloxacin; anti-viral agents such as aciclovir, ganciclovir, sidofovir and trifluorothimidine.

The effective content of the aforementioned pharmaceutical agent is different depending on a kind of a pharmaceutical agent and, generally, is preferably within a range of about 0.001 to 10 w/v %.

An application place for the antibacterial aqueous pharmaceutical composition and the aqueous pharmaceutical composition of the present invention is not particularly limited as long as it is not intravenous, but includes body cavities such as eyes, skin, rectum, urethra, nasal cavity, vagina, earhole, oral cavity and oral cave.

It is preferable that pH of the antibacterial aqueous pharmaceutical composition and the aqueous pharmaceutical composition of the present invention is 3.5 to 10. When the aqueous pharmaceutical composition of the present invention is used as an ophthalmic solution, it is preferable that pH is 4.5 or more. When pH is less than 4.5, the stimulation to eyes may become too strong. More preferably, pH is 5.5 to 8.

In order to adjust pH, pharmaceutically acceptable pH adjusting agents may be used, and examples thereof include acids such as hydrochloric acid, sulfuric acid, boric acid, phosphoric acid and acetic acid, and bases such as sodium hydroxide, monoethanolamine, diethanolamine and triethanolamine.

The antibacterial aqueous pharmaceutical composition and the aqueous pharmaceutical composition of the present invention may further contain a buffer, a salt, a preservative and a solubilizing agent which are pharmaceutical acceptable if necessary.

As the aforementioned preservative, for example, invert soaps such as benzalkonium chloride, benzethonium chloride and chlorhexidine gluconate, parabens such as methylparaben, ethylparaben, propylparaben and butylparaben, alcohols such as chlorobutanol, phenylethyl alcohol and benzyl alcohol, organic acids such as sodium dehydroacetate, sorbic acid and potassium sorbate and salts thereof may be used. In addition, a surfactant and a chelating agent may be appropriately added. These ingredients are generally used in a range of about 0.001 to 2 w/v %, preferably about 0.002 to 1 w/v %.

Examples of the aforementioned buffer include alkali metal salts of acids such as phosphoric acid, boric acid, acetic acid, tartaric acid, lactic acid and carbonic acid, amino acids such as glutamic acid, F-aminocaproic acid, aspartic acid, glycine, arginine and lysine, taurine, tris(hydroxymethylamino)methane and the like. These buffers are added to the composition at a necessary amount to maintain pH of the composition at 3.5 to 10.

Examples of the aforementioned solubilizing agent include Polysorbate 80, polyoxyethylene hydrogenated castor oil and cyclodextrin, and they are used in a range of 0 to 15 w/v %.

A method of preparing the antibacterial aqueous pharmaceutical composition and the aqueous pharmaceutical composition of the present invention is not particularly limited. For example, citrate and polyethylene glycol are added to sterile purified water to dissolve them, then pH of the solution is adjusted with a pH adjusting agent, a pharmaceutical agent as an active ingredient and optionally a preservative are added, a solution obtained by pre-dissolving methylcellulose in sterile purified water is added, pH is adjusted again, measured up with sterile purified water, and the mixture is stirred while ice-cooling. Thereafter, if necessary, various additives such as a buffer, a salt and a preservative are added. When a pharmaceutical agent is poorly soluble or insoluble, it is used by suspending it or solubilizing it with a solubilizing agent.

According to the antibacterial aqueous pharmaceutical composition and the aqueous pharmaceutical composition of the present invention, a gelation temperature can be sufficiently lowered even when new quinolone antibacterial agents such as ofloxacin are used as an active ingredient, and enhancement of the efficacy of pharmaceutical agent, reduction of a pharmaceutical agent dose, and reduction in the number of pharmaceutical agent administration time may be expected. In particular, appearance of resistant bacteria has been problematic recently for synthetic antibacterial agents and, therefore, since an antibacterial agent exhibiting the strong efficacy in a short time is desired, the present invention is suitably used when an active ingredient is a synthetic antibacterial agent.

BEST MODE FOR CARRYING OUT THE INVENTION

The present invention will be described in more detail below with reference to Examples, but is not limited to these Examples.

TEST EXAMPLE 1

[Gelation Behavior of OFLX-containing Thermally Gelling Preparation]

Methylcellulose (manufactured by Shin-Etsu Chemical, Metolose (registered trademark) SM-4, the viscosity of a 2 w/v % aqueous solution at 20° C. is 3.2 to 4.8 mPa·s) and polyethylene glycol (Macrogol 4000, manufactured by NOF Corporation) were mixed at a prescribed amount, sterile purified water heated to 85° C. was added thereto, and the mixture was stirred to disperse the ingredients. After confirmed that the ingredients were uniformly dispersed, the dispersion was ice-cooled while stirring. After confirmed that the whole became clear, prescribed amount of sodium citrate was gradually added, and was dissolved with stirring. Furthermore, a prescribed amount of ofloxacin (OFLX, final incorporation amount 0.3 w/v %) was added, and dispersed therein by stirring. To this was gradually added 1N HCl while stirring until the whole became clear. Furthermore, 1N HCl was added, pH was adjusted to 6.5, and sterile purified water was added to a prescribed volume to prepare the 0.3 w/v % OFLX thermally gelling preparation of the present invention.

Separately, the 0.3 w/v % OFLX thermally gelling preparation for comparison was prepared according to the same manner as that for the aforementioned thermally gelling preparation of the present invention except that methylcellulose was changed from SM-4 to SM-15 (manufactured by Shin-Etsu Chemical, Metolose (registered trademark), the viscosity of a 2 w/v % aqueous solution at 20° C. is 13 to 18 mPa·s).

The relationship between a temperature and the viscosity of the prepared thermally gelling preparation was studied to obtain the viscosity and a gelation temperature at 20° C. In addition, regarding the thermally gelling preparation of the present invention, a temperature at which the viscosity of the preparation becomes 100 mPa·s or more was also obtained. When the viscosity is 100 mPa·s or more, the composition can be retained on the surface of eyes for a long time even when used as an ophthalmic solution.

Measurement of the viscosity of the thermally gelling preparation was carried out as follows. The prepared OFLX-TG was placed in a stainless cup for a B type viscometer, and the cup was allowed to stand in a water bath maintained at a prescribed temperature for 3 minute. Immediately after allowing to stand, a rotor of the B type viscometer was rotated, and the viscosity of two minutes after initiation of rotor rotation was measured. The viscosity of the prepared OFLX-TG at each temperature was measured, and the viscosity at 20° C., a gelation temperature and a temperature at which the viscosity of a preparation becomes 100 mPa·s or more were obtained.

Table 1 shows formulation of the prepared preparation, the viscosities at 20° C., the gelation temperatures and the temperatures at which the viscosity of the preparation becomes 100 mPa·s or more.

The viscosity at 20° C. was lower in the thermally gelling preparation of the present invention using SM-4 at every formulation, and it was shown that the thermally gelling preparation of the present invention is more excellent than the thermally gelling preparation for comparison in that a preparation is easy to handle and the sticky feeling is small when a preparation is applied to eyes.

In addition, it was shown that the thermally gelling preparation of the preset invention using SM-4 has a lower gelation temperature as compared with the gelling preparation for comparison using SM-15, and it was found that the thermally gelling preparation of the present invention is more easily gelled by a body temperature.

TABLE 1

|  | Example | | | | | Comparative Example | | |
|---|---|---|---|---|---|---|---|---|
|  | 1 | 2 | 3 | 4 | 5 | 1 | 2 | 3 |
| SM-4 (W/V %) | 3 | 3 | 3.5 | 4 | 4 | — | — | — |
| SM-15 (W/V %) | — | — | — | — | — | 3 | 3 | 3.5 |
| Macrogol 4000 (W/V %) | 2 | 4 | 2 | 2 | 4 | 2 | 4 | 2 |
| Sodium citrate (W/V %) | 3.5 | 3.5 | 3.5 | 3.5 | 3.5 | 3.5 | 3.5 | 3.5 |
| Viscosity at 20° C. (mPa·s) | 12.9 | 12.1 | 13.4 | 15.3 | 19.6 | 55.5 | 63.6 | 70.8 |
| Gelation temperature (° C.) | 22 | 22 | 22 | 22 | 20 | 30 | 22 | 26 |
| >100 mPa·s reaching temperature (° C.) | 30 | 28 | 30 | 28 | 26 | — | — | — |

TEST EXAMPLE 2

[Gelation Behavior of LVFX-containing Thermally Gelling Preparation]

SM-4 and Macrogol 4000 were mixed at a prescribed amount, sterile purified water heated to 85° C. was added, and the ingredients were dispersed by stirring. After confirmed that the ingredients were uniformly dispersed, the dispersion was ice-cooled while stirring. After confirmed that the whole became clear, a prescribed amount of sodium citrate was gradually added, and was dissolved with stirring. Furthermore, a prescribed amount of levofloxacin (LVFX, final incorporation amount 0.5 w/v %) was added, and was dispersed by stirring. To this was added 1N NaOH to adjust pH to 7.8, and sterile purified water was added to a prescribed volume, to prepare the 0.5 w/v % LVFX thermally gelling preparation of the present invention.

As a control, sterile purified water heated to 85° C. was added to 6.0 g of SM-4, and SM-4 was dispersed by stirring. After confirmed that the ingredient was uniformly dispersed, the dispersion was ice-cooled while stirring. After confirmed that the whole became clear, 0.5 g of levofloxacin was added, and dissolved with stirring. To this was added 1N NaOH to adjust pH to 7.8, and sterile purified water was added to the total volume of 100 mL, to prepare the 0.5 w/v % LVFX thermally gelling preparation for comparison.

The relationship between a temperature and the viscosity of the prepared thermally gelling preparations was studied, and the viscosity at 20° C., a gelation temperature and a temperature at which the viscosity of a preparation becomes 100 mPa·s or more were obtained.

Table 2 shows formulations of prepared preparations, the viscosities at 20° C., the gelation temperatures and the temperatures at which the viscosity of the preparation becomes 100 mPa·s or more.

The LVFX-containing thermally gelling preparation of the present invention has the viscosity at 20° C. of less than 100 mPa·s and, therefore, it is easy to handle, and it was shown that it is gelled at 30° C. or less.

On the other hand, the LVFX-containing thermally gelling preparation for comparison containing only SM-4 has a gelation temperature of 36° C. although an incorporation amount of SM-4 is high concentration as 6.0 w/v %. In addition, a temperature at which the viscosity of a preparation becomes 100 mPa·s or more is 40° C. or more and, thus, it was shown that the thermal gelation behavior is not so good.

TABLE 2

|  | Example | | | | Com. Example |
|---|---|---|---|---|---|
|  | 6 | 7 | 8 | 9 | 4 |
| SM-4 (W/V %) | 3 | 3 | 4 | 4 | 6 |
| Macrogol 4000 (W/V %) | 2 | 4 | 2 | 4 | — |
| Sodium citrate (W/V %) | 3.5 | 3.5 | 3.5 | 3.5 | — |
| Viscosity at 20° C. (mPa·s) | 9.6 | 12 | 15.5 | 20.4 | 27.6 |
| Gelation temperature (° C.) | 24 | 22 | 22 | 20 | 36 |
| >100 mPa·s reaching temperature (° C.) | 32 | 30 | 28 | 28 | >40 |

TEST EXAMPLE 3

[Gelation Behavior of Moxifloxacin Hydrochloride-containing Thermally Gelling Preparation]

SM-4 and Macrogol 4000 were mixed at a prescribed amount, sterile purified water heated to 85° C. was added thereto, and the ingredients were dispersed by stirring. After confirmed that the ingredients were uniformly dispersed, the dispersion was ice-cooled while stirring. After confirmed that the whole became clear, a prescribed amount of sodium citrate was gradually added, and dissolved with stirring. Furthermore, a prescribed amount of moxifloxacin hydrochloride was added, and dispersed therein by stirring. To this was added 1N NaOH to adjust pH to a prescribed pH, and sterile purified water was added to a prescribed volume to prepare the moxifloxacin hydrochloride thermally gelling preparation of the present invention.

The relationship between a temperature and the viscosity of the prepared thermally gelling preparations was studied, and the viscosity at 20° C., a gelation temperature and a temperature at which the viscosity of a preparation becomes 100 mPa·s or more were obtained.

Table 3 shows formulations of the prepared preparations, the viscosities at 20° C., the gelation temperatures and the temperatures at which the viscosity of the preparation becomes 100 mPa·s or more.

In the all moxifloxacin hydrochloride thermally gelling preparation of the present invention, the viscosity at 20° C. is less than 100 mPa·s and, therefore, the preparation is easy to handle, and it was shown that the preparation is gelled at a temperature of a body temperature or less.

TABLE 3

|  | Example | |
|---|---|---|
|  | 10 | 11 |
| Pharmaceutical agent | Moxifloxacin hydrochloride | |
| Concentration (w/v %) | 0.32 | 0.32 |
| SM-4 (w/v %) | 2.8 | 3.6 |
| Macrogol 4000 (w/v %) | 4.0 | 4.0 |
| Sodium citrate (w/v %) | 3.53 | 3.53 |
| HCl | Suitable amount | Suitable amount |
| Water | Suitable amount | Suitable amount |
| pH | 7.2 | 7.2 |
| Viscosity at 20° C. (mPa·s) | 9.8 | 18.9 |
| Gelation temperature (° C.) | 24 | 22 |
| >100 mPa·s reaching temperature (° C.) | 32 | 26 |

TEST EXAMPLE 4

[Various Synthetic Antibacterial Agents-containing Thermal Gelling Preparations]

SM-4 and Macrogol 4000 were mixed at a prescribed amount, sterile purified water heated to 85° C. was added thereto, and the ingredients were dispersed by stirring. After confirmed that the ingredients were uniformly dispersed, the dispersion was ice-cooled while stirring. After confirmed that the whole became clear, a prescribed amount of citric acid was gradually added, and dissolved with stirring. Furthermore, a prescribed amount of a synthetic antibacterial agent was added, and dissolved with stirring. To this was added 1N NaOH to adjust to a prescribed pH, and sterile purified water was added to a prescribed volume, to prepare the synthetic antibacterial agent-containing thermally gelling preparation of the present invention.

The relationship between a temperature and the viscosity of the prepared thermally gelling preparations was studied, and the viscosity at 20° C., a gelation temperature and a temperature at which the viscosity of a preparation becomes 100 mPa·s or more were obtained.

Table 4 shows formulations of the prepared preparations, the viscosities at 20° C., the gelation temperatures and the temperatures at which the viscosity of the preparation becomes 100 mPa·s or more.

In the all synthetic antibacterial agent-containing thermally gelling preparation of the present invention, the viscosity at 20° C. is less than 100 mPa·s and, therefore, the preparation is easy to handle, and it was shown that the preparation is gelled at a temperature of a body temperature or less.

solved with stirring. To this was added 1N NaOH or 1N HCl to adjust to a prescribed pH, and sterile purified water was added to a prescribed volume to prepare the glaucoma treating agent-containing thermally gelling preparation of the present invention.

In addition, 2.8 g of SM-4 and 2.0 g of Macrogol 4000 were mixed, 70 mL of sterile purified water heated to 85° C. was added thereto, and the ingredients were dispersed by stirring. After confirmed that the ingredients were uniformly dispersed, the dispersion was ice-cooled while stirring. After confirmed that the whole became clear, 3.53 g of sodium citrate was gradually added, and dissolved with stirring. To this was added 1N HCl to adjust pH to 6.5, and sterile purified water was added to a volume of 100 mL to prepare the thermally gelling base. Separately, 50 mL of Rescula (registered trademark) ophthalmic solution (manufactured by Ueno Fine Chemicals) was freeze-dried. To this was added 50 mL of the aforementioned thermally gelling base, and dissolved with stirring under ice-cooling to prepare the isopropylunoproston-containing thermally gelling preparation.

Furthermore, SM-4 (4.0 g) and Macrogol 4000 (4.0 g) were mixed, 70 mL of sterile purified water heated to 85° C. was added thereto, and the ingredients were dispersed by stirring. After confirmed that the ingredients were uniformly dispersed, the dispersion was ice-cooled while stirring. After confirmed that the whole became clear, sodium citrate (3.53 g) was gradually added, and dissolved with stirring. To this was added 1N HCl to adjust pH to 7.0, and sterile purified water was added to a volume of 100 mL to obtain the thermally gelling base. Separately, 50 mL of Hypadil Kowa Ophthalmic Solution (manufactured by Kowa) was freeze-dried.

TABLE 4

| | Example | | | | |
|---|---|---|---|---|---|
| | 12 | 13 | 14 | 15 | 16 |
| Pharmaceutical agent | CPFX-HCl | NFLX | LFLX-HCl | Gatifloxacin | |
| Concentration (w/v %) | 0.3 | 0.3 | 0.3 | 0.3 | 0.3 |
| SM-4 (w/v %) | 6.0 | 6.0 | 6.0 | 4.0 | 2.8 |
| Macrogol 4000 (w/v %) | 3.0 | 3.0 | 4.0 | 4.0 | 4.0 |
| Citric acid (w/v %) | 2.3 | 2.3 | — | 2.3 | 2.3 |
| NaOH | Suitable amount | Suitable amount | Suitable amount | Suitable amount | Suitable amount |
| Water | Suitable amount | Suitable amount | Suitable amount | Suitable amount | Suitable amount |
| pH | 5.3 | 5.3 | 6.0 | 5.0 | 5.0 |
| Viscosity at 20° C. (mPa · s) | 42.0 | 37.2 | 36.0 | 17.3 | 11.3 |
| Gelation temperature (° C.) | 22 | 24 | 32 | 22 | 24 |
| >100 mPa · s reaching temperature (° C.) | 28 | 28 | 40 | 28 | 30 |

CPFX-HCl: Ciprofloxacin hydrochloride
NFLX: Norfloxacin
LFLX-HCl: Lomefloxacin hydrochloride

TEST EXAMPLE 5

[Various Glaucoma Treating Agents-containing Thermally Gelling Preparations]

SM-4 and Macrogol 4000 were mixed at a prescribed amount, sterile purified water heated to 85° C. was added thereto, and the ingredients were dispersed by stirring. After confirmed that the ingredients were uniformly dispersed, the dispersion was ice-cooled while stirring. After confirmed that the whole became clear, a prescribed amount of citric acid or sodium citrate was gradually added, and dissolved with stirring. Furthermore, a prescribed amount of glaucoma treating agent (pharmaceutical agents shown in Table 5 except for isopropylunoproston and nipradilol) was added, and dis- 50 mL of the aforementioned thermally gelling base was added thereto, and dissolved with stirring under ice-cooling to prepare the nipradilol-containing thermally gelling preparation.

The relationship between a temperature and the viscosity of prepared thermally gelling preparation was studied, and the viscosity at the 20° C., a gelation temperature and a temperature at which the viscosity of a preparation becomes 100 mPa·s or more were obtained.

Table 5 shows formulations of the prepared preparations, the viscosities at 20° C., the gelation temperatures and the temperatures at which the viscosity of a preparations becomes 100 mPa·s or more.

In the all glaucoma treating agent-containing thermally gelling preparation of the present invention, the viscosity at 20° C. is less than 100 mPa·s and, therefore, the preparation is easy to handle, and it was shown that the preparation is gelled at a temperature of body temperature or less.

and the viscosity at 20° C., a gelation temperature and a temperature at which the viscosity of a preparation becomes 100 mPa·s or more were obtained.

TABLE 5

|  | Example | | | | | | | | | | |
|---|---|---|---|---|---|---|---|---|---|---|---|
|  | 17 | 18 | 19 | 20 | 21 | 22 | 23 | 24 | 25 | 26 | 27 |
| Pharmaceutical agent | Carteolol hydrochloride | Carteolol hydrochloride | Betaxolol hydrochloride | Betaxolol hydrochloride | Timolol maleate | Timolol maleate | Timolol maleate | Pilocarpine hydrochloride | Pilocarpine hydrochloride | Isopropylunoproston | Nipraditol |
| Concentration (w/v %) | 1.0 | 1.0 | 0.56 | 0.56 | 0.68 | 0.68 | 0.68 | 1.0 | 1.0 | 0.12 | 0.25 |
| SM-4 (w/v %) | 4.0 | 4.0 | 4.0 | 2.8 | 4.0 | 2.8 | 4.0 | 5.5 | 4.0 | 2.8 | 4.0 |
| Macrogol 4000 (w/v %) | 4.0 | 4.0 | 4.0 | 4.0 | 4.0 | 4.0 | — | 4.0 | 4.0 | 2.0 | 4.0 |
| Sodium citrate (w/v %) | 3.53 | 2.0 | 3.53 | 3.53 | 3.5 | 3.53 | 3.5 | — | — | 3.53 | 3.53 |
| Citric acid (w/v%) |  |  |  |  |  |  |  | 2.3 | 2.3 | — | — |
| NaOH, HCl | Suitable amount | Suitable amount | Suitable amount | Suitable amount | Suitable amount | Suitable amount | Suitable amount | Suitable amount | Suitable amount | Suitable amount | Suitable amount |
| Water | Suitable amount | Suitable amount | Suitable amount | Suitable amount | Suitable amount | Suitable amount | Suitable amount | Suitable amount | Suitable amount | Suitable amount | Suitable amount |
| pH | 7.0 | 7.0 | 7.2 | 7.2 | 7.0 | 7.0 | 7.0 | 5.5 | 5.0 | 6.5 | 7.0 |
| Viscosity at 20° C. (mPa·s) | 18.3 | 17.6 | 17.3 | 11.5 | 20.6 | 12.6 | 13.0 | 31.6 | 18.4 | 9.8 | 22.4 |
| Gelation temperature (° C.) | 20 | 26 | 20 | 24 | 20 | 24 | 24 | 22 | 24 | 26 | 22 |
| >100 mPa·s reaching temperature (° C.) | 28 | 32 | 26 | 30 | 24 | 30 | 30 | 28 | 32 | 32 | 28 |

TEST EXAMPLE 6

[Gelation Behavior Of Various Nonsteroidal Anti-inflammatories-containing Thermally Gelling Preparations]

SM-4 and Macrogol 4000 were mixed at a prescribed amount, sterile purified water heated to 85° C. was added thereto, and the ingredients were dispersed by stirring. After confirmed that the ingredients were uniformly dispersed, the dispersion was ice-cooled by stirring. After confirmed that the whole became clear, a prescribed amount of sodium citrate was gradually added, and dissolved with stirring. A prescribed amount of an anti-inflammatory was added thereto, and dissolved therein, followed by well mixing. Furthermore, 1N NaOH or 1N HCl was added to adjust to a prescribed pH, and sterile purified water was added to a prescribed volume to prepare the non-steroidal anti-inflammatory treating agent-containing thermally gelling preparation of the present invention.

The relationship between a temperature and the viscosity of the prepared thermally gelling preparations was studied, and the viscosities at 20° C., the gelation temperatures and the temperatures at which the viscosity of a preparations becomes 100 mPa·s or more.

In the all nonsteroidal anti-inflammatory-containing thermally gelling preparation of the present invention, the viscosity at 20° C. is less than 100 mPa·s and, therefore, the preparation is easy to handle, and it was shown that the preparation is gelled at a temperature of a body temperature or less.

TABLE 6

|  | Example | | | | | |
|---|---|---|---|---|---|---|
|  | 28 | 29 | 30 | 31 | 32 | 33 |
| Pharmaceutical agent | Bromfenac sodium | Bromfenac sodium | Pranoprofen | Pranoprofen | Diclofenac sodium | Diclofenac sodium |
| Concentration (w/v %) | 0.1 | 0.1 | 0.1 | 0.1 | 0.1 | 0.1 |
| SM-4 (w/v %) | 4.0 | 2.8 | 4.0 | 2.8 | 2.8 | 2.8 |
| Macrogol 4000 (w/v %) | 4.0 | 4.0 | 4.0 | 4.0 | 4.0 | 2.0 |
| Sodium citrate (w/v %) | 3.53 | 3.53 | 3.53 | 3.53 | 3.53 | 3.53 |
| NaOH, HCl | Suitable amount | Suitable amount | Suitable amount | Suitable amount | Suitable amount | Suitable amount |
| Water | Suitable amount | Suitable amount | Suitable amount | Suitable amount | Suitable amount | Suitable amount |
| pH | 8.3 | 8.3 | 7.5 | 7.5 | 6.8 | 6.8 |
| Viscosity at 20° C. (mPa·s) | 17.2 | 9.5 | 18.9 | 10.3 | 11.8 | 5.3 |
| Gelation temperature (° C.) | 20 | 22 | 20 | 22 | 22 | 24 |
| >100 mPa·s reaching temperature (° C.) | 26 | 30 | 26 | 30 | 28 | 32 |

TEST EXAMPLE 7

[Gelation Behavior of Various Anti-allergic Agents-containing Thermally Gelling Preparations]

SM-4 and Macrogol 4000 were mixed at a prescribed amount, sterile purified water heated to 85° C. was added thereto, and the ingredients were dispersed by stirring. After confirmed that the ingredients were uniformly dispersed, the dispersion was ice-cooled while stirring. After confirmed that the whole became clear, a prescribed amount of sodium citrate was gradually added, and dissolved with stirring. Furthermore, a prescribed amount of anti-allergic agent was added, and dissolved with stirring. To this was added 1N NaOH or 1N HCl to adjust to a prescribed pH, and sterile purified water was added to a prescribed volume to prepare the anti-allergic agent-containing thermally gelling preparation of the present invention.

The relationship between a temperature and the viscosity of the prepared thermally gelling preparations was studied, and the viscosity at 20° C., a gelation temperature and a temperature at which the viscosity of a preparation becomes 100 mPa·s or more were obtained.

Table 7 shows formulations of the prepared preparations, the viscosities at 20° C., the gelation temperatures and the temperatures at which the viscosity of the preparation becomes 100 mPa·s or more.

In the all anti-allergic agent-containing thermally gelling preparation of the present invention, the viscosity at 20° C. is less than 100 mPa·s and, therefore, the preparation is easy to handle, and it was shown that the preparation is gelled at a temperature of a body temperature or less.

purified water was added to a prescribed volume to prepare the betamethasone sodium phosphate-containing thermally gelling preparation of the present invention.

In addition, SM-4 and Macrogol 4000 were mixed at a prescribed amount, sterile purified water heated to 85° C. was added thereto, and the ingredients were dispersed by stirring. After confirmed that the ingredients were uniformly dispersed, the dispersion was ice-cooled while stirring. After confirmed that the whole became clear, a prescribed amount of sodium citrate was gradually added, and dissolved with stirring. To this was added 1N NaOH or 1N HCl to adjust to a prescribed pH, and sterile purified water was added to a prescribed volume to prepare the thermally gelling base. To this was added a prescribed amount of fluorometholone or prednisolone acetate, and the ingredients were uniformly dispersed to prepare the steroidal anti-inflammatory treating agent-containing thermally gelling preparation of the present invention.

The relationship between a temperature and the viscosity of the prepared thermally gelling preparations was studied, and the viscosity at 20° C., a gelation temperature and a

TABLE 7

| | Example | | | | |
|---|---|---|---|---|---|
| | 34 | 35 | 36 | 37 | 38 |
| Pharmaceutical agent | Ketotifen fumarate | Acitazanolast | Disodium cromoglicate | | Tranilast |
| Concentration (w/v %) | 0.069 | 0.1 | 0.75 | 0.75 | 0.5 |
| SM-4 (w/v %) | 4.0 | 2.8 | 2.8 | 6.0 | 6.0 |
| Macrogol 4000 (w/v %) | 4.0 | 4.0 | 4.0 | 6.0 | 6.0 |
| Sodium citrate (w/v %) | 3.53 | 3.53 | 3.0 | — | — |
| NaOH, HCl | Suitable amount | Suitable amount | Suitable amount | Suitable amount | Suitable amount |
| Water | Suitable amount | Suitable amount | Suitable amount | Suitable amount | Suitable amount |
| pH | 6.5 | 7.0 | 7.0 | 7.0 | 7.5 |
| Viscosity at 20° C. (mPa · s) | 18.9 | 11.0 | 11.4 | 54.6 | 50.3 |
| Gelation temperature (° C.) | 20 | 26 | 24 | 26 | 26 |
| >100 mPa · s reaching temperature (° C.) | 26 | 34 | 32 | 32 | 32 |

TEST EXAMPLE 8

[Gelation Behavior of Various Steroidal Anti-inflammatory Agents-containing Thermally Gelling Preparations]

SM-4 and Macrogol 4000 were mixed at a prescribed amount, sterile purified water heated to 85° C. was added thereto, and the ingredients were dispersed by stirring. After confirmed that the ingredients were uniformly dispersed, the dispersion was ice-cooled while stirring. After confirmed that the whole became clear, a prescribed amount of sodium citrate was gradually added, and dissolved with stirring. Furthermore, a prescribed amount of betamethasone sodium phosphate was added, and dissolved with stirring. To this was added 1N NaOH or 1N HCl to adjust to pH 8.0, and sterile temperature at which the viscosity of a preparation becomes 100 mPa·s or more were obtained.

Table 8 shows formulations of the prepared preparations, the viscosities at 20° C., the gelation temperatures and the temperatures at which the viscosity of the preparation becomes 100 mPa·s or more.

In the all steroidal anti-inflammatory treating agent-containing thermally gelling preparation of the present invention, the viscosity at 20° C. is less than 100 mPa·s and, therefore, the preparation is easy to handle, and it was shown that the preparation is gelled at a temperature of a body temperature or less.

TABLE 8

| | Example | | | | | |
|---|---|---|---|---|---|---|
| | 39 | 40 | 41 | 42 | 43 | 44 |
| Pharmaceutical agent | Bethamethasone sodium phosphate | | Prednisolone acetate | | Fluorometolone | |
| Concentration (w/v %) | 0.01 | 0.01 | 0.11 | 0.11 | 0.1 | 0.1 |

TABLE 8-continued

| | Example | | | | | |
|---|---|---|---|---|---|---|
| | 39 | 40 | 41 | 42 | 43 | 44 |
| SM-4 (w/v %) | 2.8 | 4.0 | 2.8 | 4.0 | 2.8 | 4.0 |
| Macrogol 4000 (w/v %) | 4.0 | 4.0 | 4.0 | 4.0 | 4.0 | 4.0 |
| Sodium citrate (w/v %) | 3.53 | 3.53 | 3.53 | 3.53 | 3.53 | 3.53 |
| NaOH, HCl | Suitable amount | Suitable amount | Suitable amount | Suitable amount | Suitable amount | Suitable amount |
| Water | Suitable amount | Suitable amount | Suitable amount | Suitable amount | Suitable amount | Suitable amount |
| pH | 8.0 | 8.0 | 6.0 | 6.0 | 7.0 | 7.0 |
| Viscosity at 20° C. (mPa · s) | 10.4 | 18.9 | 10.2 | 20.3 | 12.2 | 19.1 |
| Gelation temperature (° C.) | 22 | 20 | 22 | 20 | 22 | 20 |
| >100 mPa · s reaching temperature (° C.) | 30 | 26 | 30 | 26 | 28 | 26 |

TEST EXAMPLE 9

[Gelation Behavior of Various Agents-containing Thermally Gelling Preparations]

SM-4 and Macrogol 4000 were mixed at a prescribed amount, sterile purified water heated to 85° C. was added thereto, and the ingredients were dispersed by stirring. After confirmed that the ingredients were uniformly dispersed, the dispersion was ice-cooled while stirring. After confirmed that the whole became clear, a prescribed amount of sodium citrate or citric acid was gradually added, and dissolved with stirring. Furthermore, a prescribed amount of fluorescein sodium, gentamicin sulfate or pirenoxine was added, and dissolved with stirring. To this was added 1N or 5N NaOH or 1N HCl to adjust to a prescribed pH, and sterile purified water was added to a prescribed volume to prepare the pharmaceutical agent-containing thermally gelling preparation of the present invention.

In addition, SM-4 and Macrogol 4000 were mixed at a prescribed amount, sterile purified water heated to 85° C. was added thereto, and the ingredient were dispersed by stirring. After confirmed that the ingredients were uniformly dispersed, the dispersion was ice-cooled while stirring. After confirmed that the whole became clear, a prescribed amount of sodium citrate or citric acid was gradually added, and dissolved with stirring. To this was added 1N NaOH or 1N HCl to adjust to a prescribed pH, and sterile purified water was added to a prescribed volume to prepare the thermally gelling base. To this was added a prescribed amount of ciclosporin A or aciclovir, and dispersed uniformly therein to prepare the pharmaceutical agent-containing thermally gelling preparation of the present invention.

The relationship between a temperature and the viscosity of the prepared thermally gelling preparations was studied, and the viscosity at 20° C., a gelation temperature and a temperature at which the viscosity of a preparation becomes 100 mPa·s or more were obtained.

Table 9 shows formulations of the prepared preparations, the viscosities at 20° C., the gelation temperatures and the temperatures at which the viscosity of the preparation becomes 100 mPa·s or more.

In the all various pharmaceutical agents-containing thermally gelling preparations of the present invention, the viscosity at 20° C. is less than 100 mPa·s and, therefore, the preparation is easy to handle, and it was shown that the preparation is gelled at a temperature of a body temperature or less.

TABLE 9

| | Example | | |
|---|---|---|---|
| | 45 | 46 | 47 |
| Pharmaceutical agent | Fluorescein sodium | Gentamicin sulfate | Pirenoxine |
| Concentration (w/v %) | 0.01 | 0.3 (Titer) | 0.005 |
| SM-4 (w/v %) | 3.2 | 3.2 | 6.5 |
| Macrogol 4000 (w/v %) | 4.0 | 4.0 | 3.0 |
| Sodium citrate (w/v %) | 3.53 | 3.53 | — |
| Citric acid (w/v %) | — | — | 2.3 |
| NaOH, HCl | Suitable amount | Suitable amount | Suitable amount |
| Water | Suitable amount | Suitable amount | Suitable amount |
| pH | 7.4 | 7.0 | 4.0 |
| Viscosity at 20° C. (mPa · s) | 13.1 | 11.8 | 55.7 |
| Gelation temperature (° C.) | 22 | 22 | 24 |
| >100 mPa · s reaching temperature (° C.) | 28 | 28 | 28 |

| | Example | |
|---|---|---|
| | 48 | 49 |
| Pharmaceutical agent | Cyclosporin A | Acyclovir |
| Concentration (w/v %) | 0.1 | 3.0 |
| SM-4 (w/v %) | 3.2 | 2.8 |
| PEG-4000 (w/v %) | 4.0 | 4.0 |
| Sodium citrate (w/v %) | 3.53 | 3.53 |
| NaOH, HCl | Suitable amount | Suitable amount |
| Water | Suitable amount | Suitable amount |
| pH | 7.0 | 7.0 |
| Viscosity at 20° C. (mPa · s) | 12.6 | 12.3 |
| Gelation temperature (° C.) | 22 | 20 |
| >100 mPa · s reaching temperature (° C.) | 28 | 30 |

TEST EXAMPLE 10

[Gelation Behavior of Thermally Gelling Preparation Containing 2 or More Pharmaceutical Agents]

SM-4 and Macrogol 4000 were mixed at a prescribed amount, sterile purified water heated to 85° C. was added thereto, and the ingredients were dispersed by stirring. After confirmed that the ingredients were uniformly dispersed, the dispersion was ice-cooled while stirring. After confirmed that the whole became clear, a prescribed amount of sodium citrate or citric acid was gradually added, and dissolved with stirring. Furthermore, a prescribed amount of pharmaceutical agent was added, and dissolved with stirring. To this was added 1N NaOH or 1N HCl to adjust to a prescribed pH, sterile purified water was added to a prescribed volume to prepare the thermally gelling preparation of the present invention containing 2 or more pharmaceutical agents.

The relationship between a temperature and the viscosity of the prepared thermally gelling preparations was studied, and the viscosity at 20° C., a gelation temperature and a temperature at which the viscosity of a preparation becomes 100 mPa·s or more were obtained.

Table 10 shows formulations of the prepared preparations, the viscosities at 20° C., the gelation temperatures and the temperatures at which the viscosity of preparations becomes 100 mPa·s or more.

In the all various pharmaceutical agents-containing thermally gelling preparations of the present invention, the viscosity at 20° C. is less than 100 mPa·s and, therefore, the preparation is easy to handle, and it was shown that the preparation is gelled at a temperature of a body temperature or less.

The prepared OFLX-TG was placed in a stainless cup for a B type viscometer, and the cup was inserted into a water bath maintained at 30° C. or 34° C. Immediately, a rotor of the B type viscometer was rotated, and the viscosity was measured every 30 seconds from initiation of rotor rotation. A time point at which the viscosity became the lowest was regarded as gelation initiating time, and the viscosity was measured 5 minutes after gelation initiation. From this, the viscosity which had risen for 5 minutes from gelation initiation was obtained, and further the viscosity risen per minute was obtained, which was regarded as a thermal gelling rate.

Table 11 shows OFLX-TG formulation and a thermal gelling rate at 30° C. or 34° C. As a result, at any formulation, it was shown that the thermally gelling preparation of the present invention using SM-4 has a rapid thermal gelling rate as compared with a preparation for comparison. For example, in the case of an ophthalmic solution, an applied pharmaceutical agent solution is discharged rapidly from the surface of eyes. Therefore, an ophthalmic solution which is gelled as rapid as possible on the surface of eyes is a more preferable

TABLE 10

| | Example | | |
|---|---|---|---|
| | 50 | 51 | 52 |
| Pharmaceutical agent | 0.1 w/v % Diclofenac sodium 0.5 w/v % LVFX — | 0.1 w/v % Diclofenac sodium 0.5 w/v % LVFX 0.1 w/v % Betamethazone sodium phosphate | 0.5 w/v % Tropicamide 0.5 w/v % Phenylephrine hydrochloride — |
| SM-4 (w/v %) | 2.8 | 3.2 | 5.0 |
| Macrogol 4000 (w/v %) | 4.0 | 4.0 | 4.0 |
| Sodium citrate (w/v %) | 3.53 | 3.53 | — |
| Citric acid (w/v %) | — | — | 2.3 |
| NaOH, HCl | Suitable amount | Suitable amount | Suitable amount |
| Water | Suitable amount | Suitable amount | Suitable amount |
| pH | 7.5 | 7.0 | 5.5 |
| Viscosity at 20° C. (mPa · s) | 8.4 | 11.8 | 23.8 |
| Gelation temperature (° C.) | 24 | 22 | 24 |
| >100 mPa · s reaching temperature (° C.) | 30 | 28 | 30 |

TEST EXAMPLE 11

[Viscosity Rising Rate (Thermal Gelling Rate) Test]

A prescribed amount of SM-4 and 2.0 g of Macrogol 4000 were mixed, sterile purified water heated to 85° C. was added thereto, and the ingredients were dispersed by stirring. After confirmed that the ingredients were uniformly dispersed, the dispersion was ice-cooled while stirring. After confirmed that the whole became clear, a prescribed amount of sodium citrate was gradually added, and dissolved therein. Furthermore, 0.3 g of OFLX was added, and uniformly dispersed therein. To this was gradually added 1N HCl under stirring until OFLX was dissolved.

After confirmed that the solution became clear, pH was adjusted to 6.5 with 1N HCl, and sterile purified water was added to a total volume of 100 mL to prepare the OFLX-containing thermally gelling preparation (OFLX-TG) of the present invention.

As a comparison, a prescribed amount of SM-15 and 4.0 g of Macrogol 4000 were mixed, and the same procedures as those for the aforementioned OLFX-TG of the present invention were performed to prepare OLFX-TG for comparison.

The prepared OFLX-TG was retained at a constant temperature, and the relationship between a retention time and the viscosity was studied. Measurement of a thermal gelling rate of OFLX-TG was performed as follows.

thermally gelling preparation because a discharging rate of a pharmaceutical agent solution is delayed. It was shown that the thermally gelling preparation of the present invention using SM-4 has a rapid thermal gelling rate as compared with the thermally gelling preparation for comparison and, thus, is a more preferable preparation.

TABLE 11

| | Example | | Comparative Example | |
|---|---|---|---|---|
| | 53 | 54 | 5 | 6 |
| OFLX (w/v %) | 0.3 | 0.3 | 0.3 | 0.3 |
| SM-4 (w/v %) | 2.3 | 2.5 | — | — |
| SM-15 (w/v %) | — | — | 2.3 | 2.5 |
| Macrogol 4000 (w/v %) | 2.0 | 2.0 | 2.0 | 2.0 |
| Sodium citrate (w/v %) | 3.53 | 2.5 | 3.53 | 2.5 |
| HCl | Suitable amount | Suitable amount | Suitable amount | Suitable amount |
| Water | Suitable amount | Suitable amount | Suitable amount | Suitable amount |
| pH | 6.5 | 6.5 | 6.5 | 6.5 |
| Thermal gelling rate viscosity | | | | |
| 30° C. (mPa · s/min) | 1.7 | 0.2 | 0.3 | 0.1 |
| 34° C. (mPa · s/min) | 11.4 | 1.7 | 6.3 | 0.5 |

REFERENCE EXAMPLE

[Gelation Behavior of Thermally Gelling Base Containing an Acid other than Citric Acid]

SM-4 and Macrogol 4000 were mixed at a prescribed amount, sterile purified water heated to 85° C. was added thereto, and the ingredients were dispersed by stirring. After confirmed that the ingredients were uniformly dispersed, the dispersion was ice-cooled while stirring. After confirmed that the whole became clear, a prescribed amount of each of a variety of acids shown in Table 12 was gradually added, and dissolved with stirring. Furthermore, after pH was adjusted to 7.5 with 1N NaOH or 1N HCl, sterile purified water was added to a prescribed volume to prepare each of the thermally gelling base containing each of a variety of acids of the present invention.

Separately, a thermally gelling base for comparison containing no acid was prepared according to the same manner as that for the thermally gelling base containing each of the aforementioned variety of acids.

The relationship between a temperature and the viscosity of the prepared thermally gelling bases was studied, and the viscosity at 20° C., a gelation temperature and a temperature at which the viscosity of a preparation becomes 100 mPa·s or more were obtained.

Table 12 shows formulations of the prepared preparations, the viscosities at 20° C., the gelation temperatures and the temperatures at which the viscosity of the preparation becomes 100 mPa·s or more.

As compared with the thermally gelling preparation for comparison containing no acid, it was shown that the thermally gelling base containing each of acids shown in Table 12 has a lower gelation temperature and a lower temperature at which the viscosity of a preparation becomes 100 mPa·s or more, and thus it is a preparation which is easily gelled. From this, it was suggested that, when the thermally gelling preparation using the thermally gelling base containing each of acids shown in Table 12 is administered, the higher bioavailability can be obtained.

TEST EXAMPLE 12

<Preparing Procedure of a Preparation>

SM-4 (4.0 g) and Macrogol 4000 (4.0 g) were mixed, sterile purified water heated to 85° C. was added thereto, and the ingredients were dispersed by stirring. After the ingredients were uniformly dispersed, the dispersion was ice-cooled while stirring. After confirmed that the whole became clear, sodium citrate (3.53 g) was gradually added, and dissolved with stirring.

Furthermore, 0.5 g of levofloxacin (LVFX) was added, and dissolved with stirring. To this was added 1N NaOH to adjust to pH 7.8, and sterile purified water was added to a total volume of 100 mL to prepare the LVFX thermally gelling preparation (LVFX-TG) of the present invention.

As a comparison, 1.5 g of SM-15, 0.4 g of Metolose (registered trademark) SM-400 (methylcellulose manufactured by Shin-Etsu Chemical Industries), the viscosity of a 2 w/v % aqueous solution at 20° C. is 350 to 550 mPa·s) and 4.0 g of Macrogol 4000 were mixed, and the same procedures as those for the aforementioned present LVFX-TG were performed to obtain LVFX-TG for comparison.

The relationship between a temperature and the viscosity of the prepared LVFX-TG was studied. In the LVFX-TG of the present invention, the viscosity at 20° C. was 19.3 mPa·s, a gelation temperature was 22° C. and a temperature at which the viscosity of a preparation becomes 100 mPa·s or more was 26° C. On the other hand, in the LVFX-TG for comparison, the viscosity at 20° C. was 38.1 mPa·s, a gelation temperature was 30° C. and a temperature at which the viscosity of a preparation becomes 100 mPa·s or more was 34° C.

<Test to Examine the Transition of LVFX-TG or CRAVIT Ophthalmic Solution into Rabbit Conjunctiva and Aqueous Humor>

Each 50 µL of the prepared LVFX-TG or CRAVIT ophthalmic solution (manufactured by Santen Pharmaceutical Co., Ltd., containing 0.5% LVFX) was instilled to Japanese White rabbit (male, body weight: 2.3 to 2.8 kg), and then the

TABLE 12

| Kind of acid | Aspartic acid | Sodium glutamate | Sodium lactate | Sodium gluconate | — | Succinic acid | Maleic acid |
|---|---|---|---|---|---|---|---|
| Concentration (w/v %) | 3.0 | 3.0 | 2.9 | 2.6 | — | 2.3 | 2.3 |
| SM-4 (w/v %) | 6.0 | 6.0 | 6.0 | 6.0 | 6.0 | 4.0 | 4.0 |
| PEG4000 (w/v %) | 4.0 | 4.0 | 4.0 | 4.0 | 4.0 | 4.0 | 4.0 |
| NaOH, HCl | Suitable amount | Suitable amount | Suitable amount | Suitable amount | Suitable amount | Suitable amount | Suitable amount |
| Water | Suitable amount | Suitable amount | Suitable amount | Suitable amount | Suitable amount | Suitable amount | Suitable amount |
| pH | 7.5 | 7.5 | 7.5 | 7.5 | 7.5 | 7.5 | 7.5 |
| Viscosity at 20° C. (mPa·s) | 51.5 | 43.6 | 57.0 | 49.5 | 44.0 | 22.5 | 18.1 |
| Gelation temperature (° C.) | <25 | <25 | <25 | <25 | 32 | <25 | <25 |
| >100 mPa·s reaching temperature (° C.) | <29 | <29 | <29 | <29 | 40 | <29 | <29 |

| Kind of acid | Sodium fumarate | — | Sodium malate | Sodium tartarate | — |
|---|---|---|---|---|---|
| Concentration (w/v %) | 2.7 | — | 3.1 | 3.0 | — |
| SM-4 (w/v %) | 4.0 | 4.0 | 3.6 | 3.6 | 3.6 |
| SM-100 (w/v %) | | | 0.4 | 0.4 | 0.4 |
| PEG4000 (w/v %) | 4.0 | 4.0 | 4.0 | 4.0 | 4.0 |
| NaOH, HCl | Suitable amount | Suitable amount | Suitable amount | Suitable amount | Suitable amount |
| Water | Suitable amount | Suitable amount | Suitable amount | Suitable amount | Suitable amount |
| pH | 7.5 | 7.5 | 7.5 | 7.5 | 7.5 |
| Viscosity at 20° C. (mPa·s) | 34.7 | 16.3 | 28.5 | 39.1 | 44.0 |
| Gelation temperature (° C.) | <25 | 34 | <25 | <25 | 29 |
| >100 mPa·s reaching temperature (° C.) | <29 | >40 | <29 | <29 | 35 |

LVFX concentrations in conjunctiva and aqueous humor were determined at 1, 2 and 4 hours after administration.

The concentration of LVFX in conjunctiva was obtained as follows. The taken conjunctiva was transferred into a spit tube containing physiological saline, and conjunctiva was washed by inversion stirring. The washed conjunctiva was homogenized, LVFX was extracted with an organic solvent, and determined by HPLC.

The concentration of LVFX in aqueous humor was obtained by filtering the aqueous humor with a filter and analyzing the filtrate by HPLC.

The resulting LVFX concentrations in conjunctiva and aqueous humor are shown in Tables 13 and 14, respectively.

The LVFX-TG of the present invention showed a significantly higher value of the LVFX concentration in conjunctiva at any time of 1, 2 and 4 hours after administration, as compared with LVFX-TG for comparison and CRAVIT ophthalmic solution. In addition, the LVFX-TG of the present invention showed a significantly higher value of the LVFX concentration in aqueous humor at any time of 1, 2 and 4 hours after administration, as compared with CRAVIT ophthalmic solution, and showed a significantly higher value at 1 hour after administration as compared with LVFX-TG for comparison.

From this, it was shown that the LVFX-TG of the present invention has the much higher penetrating property of pharmaceutical agent into eye tissues than LVFX-TG prepared in Japanese Patent No. 2729859 or a commercially available ophthalmic solution, and is preferable as an ophthalmic solution.

TABLE 13

Concentration of LVFX in conjunctiva after administration of levofloxacin (LVFX) thermo-setting gel ophthalmic solution or CRAVIT ophthalmic solution to albino rabbits (μg/g, n = 4 to 6)[1]

| Ophthalmic solution | | Hours after application | | |
|---|---|---|---|---|
| | | 1 hr | 2 hr | 4 hr |
| LVFX-TG of the present invention | Average | 9.10##** | 1.18#* | 0.46##* |
| | ±SD | 3.74 | 0.66 | 0.25 |
| LVFX-TG for comparison | Average | 1.40 | 0.18 | 0.08 |
| | ±SD | 0.66 | 0.02 | 0.06 |
| CRAVIT ophthalmic solution | Average | 1.46 | 0.17 | 0.12 |
| | ±SD | 1.14 | 0.06 | 0.08 |

[1]50 μL of any of three kinds of different LVFX ophthalmic solutions was instilled to right eye of the same rabbit, and 50 μL of LVFX ophthalmic solution different from that for right eye was instilled to left eye.
*$p < 0.05$,
**$p < 0.01$ (LVFX-TG of the present invention vs CRAVIT ophthalmic solution)
$p < 0.05$,
$p < 0.01$ (LVFX-TG of the present invention vs LVFX-TG for comparison) Tukey-kramer test

TABLE 14

Concentration of LVFX in aqueous humor after administration of levofloxacin (LVFX) thermo-setting gel ophthalmic solution or CRAVIT ophthalmic solution to albino rabbits (μg/mL, n = 5 to 6)[1]

| Ophthalmic solution | | Hours after application | | |
|---|---|---|---|---|
| | | 1 hr | 2 hr | 4 hr |
| LVFX-TG of the present invention | Average | 2.297#** | 2.174** | 0.509* |
| | ±SD | 0.614 | 0.885 | 0.243 |
| LVFX-TG for comparison | Average | 1.538 | 1.495 | 0.297 |
| | ±SD | 0.407 | 0.801 | 0.085 |
| CRAVIT ophthalmic solution | Average | 1.341 | 0.710 | 0.231 |
| | ±SD | 0.159 | 0.289 | 0.060 |

[1]50 μL of any of three kinds of different LVFX ophthalmic solutions was instilled to right eye of the same rabbit, and 50 μL of LVFX ophthalmic solution different from that for right eye was instilled to left eye.
*$p < 0.05$,
**$p < 0.01$ (LVFX-TG of the present invention vs CRAVIT ophthalmic solution)
$p < 0.05$,
$p < 0.01$ (LVFX-TG of the present invention vs LVFX-TG for comparison) Tukey-kramer test

TEST EXAMPLE 13

[Test to Examine the Penetration of LVFX-containing Thermo-setting Gel Preparations Having Different Gelation Temperatures into Rabbit Eye Tissue]

<Preparing Procedure of a Preparation>

SM-4 (4.0 g) and Macrogol 4000 (4.0 g) were mixed, 70 mL of sterile purified water heated to 85° C. was added thereto, and the ingredients were dispersed by stirring. After confirmed that the ingredients were uniformly dispersed, the dispersion was ice-cooled while stirring. After confirmed that the whole became clear, 3.53 g of sodium citrate was gradually added, and dissolved with stirring. Furthermore, 0.5 g of levofloxacin (LVFX) was added, and dissolved with stirring. To this was added 1N NaOH to adjust to pH 7.8, and sterile purified water was added to a volume of 100 mL to prepare the 0.5 w/v % LVFX thermally gelling preparation (LVFX-TG, Preparation A) of the present invention.

In the prepared Preparation A, the viscosity at 20° C. was 20.1 mPa·s, a gelation temperature was 20° C., a temperature at which the viscosity of a preparation becomes 100 mPa·s or more was 26° C.

Separately, SM-4 (2.8 g) and Macrogol 4000 (4.0 g) were mixed, and the same procedures as those for the aforementioned preparation A were performed to prepare the 0.5 w/v % LVFX-TG (Preparation B) of the present invention.

In the prepared Preparation B, the viscosity at 20° C. was 12.1 mPa·s, a gelation temperature was 24° C., and a temperature at which the viscosity of a preparation becomes 100 mPa·s or more was 32° C.

<Test to Examine the Penetration of Levofloxacin (LVFX) Thermo-setting Gel Ophthalmic Solution or CRAVIT Ophthalmic Solution into the Surface of Conjunctiva, in Conjunctiva and in Aqueous Humor of Rabbit>

Each 50 μL of two formulations of the prepared LVFX-TG (Preparation A and Preparation B) or CRAVIT ophthalmic solution (manufactured by Santen Pharmaceutical Co., Ltd., containing 0.5% LVFX) was instilled to Japanese White rabbit (male, body weight: 2.1 to 2.6 kg), and the LVFX concentrations in conjunctiva, on the surface of conjunctiva and in aqueous humor were determined at 1 and 2 hours after administration.

The concentration of LVFX in conjunctiva was obtained according to the same manner as that in Test Example 12.

The concentration of LVFX on the surface of conjunctiva was obtained as follows. LVFX dissolved in physiological saline after conjunctiva washing was extracted with an organic solvent, and measured by HPLC. Then, the amount of LVFX which had been dissolved in conjunctiva wash (physiological saline) was calculated, converted into the amount per 1 g of taken conjunctiva, and the resulting value was adopted as the LVFX concentration on the surface of conjunctiva.

The concentration of LVFX in aqueous humor was obtained according to the same manner as that of Test Example 12.

The resulting LVFX concentrations in conjunctiva, on the surface of conjunctiva and in aqueous humor are shown in Tables 15, 16 and 17, respectively.

TABLE 15

Concentrations in conjunctiva after administration of levofloxacin (LVFX) thermo-setting gel ophthalmic solution or CRAVIT ophthalmic solution to albino rabbits (μg/g, n = 4 to 6)

| Ophthalmic solution | | Hours after application | |
|---|---|---|---|
| | | 1 hr | 2 hr |
| Preparation A | Average | 8.49* | 1.20** |
| | ±SD | 4.84 | 0.54 |
| Preparation B | Average | 10.56** | 1.24** |
| | ±SD | 4.09 | 0.40 |
| CRAVIT ophthalmic solution | Average | 0.18 | 0.12 |
| | ±SD | 0.06 | 0.05 |

*$p < 0.05$,
**$p < 0.01$ (vs CRAVIT ophthalmic solution) Tukey-kramer test

From the results in Table 15, the concentrations of LVFX in conjunctiva at 1 and 2 hours after administration of Preparation A and Preparation B formulations showed a significantly higher value at any time as compared with CRAVIT ophthalmic solution.

TABLE 16

Concentrations on the surface of conjunctiva after application of levofloxacin (LVFX) thermo-setting gel ophthalmic solution or CRAVIT ophthalmic solution to albino rabbits (μg/g, n = 4 to 5)

| Ophthalmic solution | | Hours after application | |
|---|---|---|---|
| | | 1 hr | 2 hr |
| Preparation A | Average | 6.17 | 0.98 |
| | ±SD | 5.61 | 1.71 |
| Preparation B | Average | 5.33 | 1.51 |
| | ±SD | 2.78 | 1.81 |
| CRAVIT ophthalmic solution | Average | 0.58 | 0.20 |
| | ±SD | 0.41 | 0.25 |

From the results of Table 16, the concentrations of LVFX on the surface of conjunctiva at 1 hour after administration of Preparation A and Preparation B formulations showed a clearly higher values which are 10.6- and 9.2-fold the value of CRAVIT ophthalmic solution, respectively. In addition, also at 2 hours after administration, they showed clearly higher values which are 4.9- and 7.6-fold the value of CRAVIT ophthalmic solution, respectively.

TABLE 17

Concentrations in aqueous humor after administration of levofloxacin (LVFX) thermo-setting gel ophthalmic solution or CRAVIT ophthalmic solution to albino rabbits (μg/mL, n = 5)

| Ophthalmic solution | | Hours after application | |
|---|---|---|---|
| | | 1 hr | 2 hr |
| Preparation A | Average | 2.981** | 1.986** |
| | ±SD | 0.737 | 0.767 |
| Preparation B | Average | 2.361* | 1.842** |
| | ±SD | 0.670 | 0.307 |
| CRAVIT ophthalmic solution | Average | 1.292 | 0.709 |
| | ±SD | 0.209 | 0.216 |

*$p < 0.05$,
**$p < 0.01$ (vs CRAVIT ophthalmic solution) Tukey-Kramer test

From the results of Table 17, the concentrations of LVFX in aqueous humor at 1 and 2 hours after administration of Preparation A and Preparation B formulations showed significantly higher values at any time as compared with CRAVIT ophthalmic solution.

From the above results, it was shown that, on the surface of conjunctiva, in conjunctiva and in aqueous humor, the higher concentration of LVFX remains over a long time of 2 or more hours when Preparation A or Preparation B formulation is administered than when a commercially available ophthalmic solution of CRAVIT is administered. In addition, from this, it was shown that Preparation A and Preparation B formulations have the far higher antibacterial effects as compared with CRAVIT ophthalmic solution which is a commercially available ophthalmic solution.

TEST EXAMPLE 14

[Test to Examine the Transition of OFLX-containing Thermo-setting Gel Preparations Having Different Gelation Temperatures into Rabbit Eye Tissue]

<Preparing Procedure of OFLX-containing Thermally Gelling Preparation>

SM-4 (4.0 g) and Macrogol 4000 (4.0 g) were mixed, 70 mL of sterile purified water heated to 85° C. was added, and the ingredients were dispersed by stirring. After confirmed that the ingredients were uniformly dispersed, the dispersion was ice-cooled while stirring. After confirmed that the whole became clear, sodium citrate (3.53 g) was gradually added, and dissolved with stirring. Furthermore, 0.3 g of ofloxacin (OFLX) was added, and dispersed by stirring. To this was gradually added 1N HCl while stirring until the whole became clear. Furthermore, 1N HCl was added to adjust to pH 6.5, and sterile purified water was added to a volume of 100 mL to prepare the 0.3 w/v % OFLX thermally gelling preparation (OFLX-TG, Preparation C).

In the prepared preparation C, the viscosity at 20° C. was 19.3 mPa·s, a gelation temperature was 22° C., a temperature at which the viscosity of a preparation becomes 100 mPa·s or more was 26° C.

Separately, SM-4 (2.8 g) and Macrogol 4000 (4.0 g) were mixed, and the same procedures as those for the aforementioned preparation C were performed to obtain the 0.3 w/v % OFLX-TG (Preparation D).

In the prepared Preparation D, the viscosity at 20° C. was 11.0 mPa·s, a gelation temperature was 24° C., and a temperature at which the viscosity of a preparation becomes 100 mPa·s or more was 30° C.

Furthermore, as comparison, 0.4 g of SM-400, 1.5 g of SM-15 and 4.0 g of Macrogol 4000 were mixed, and the same procedures as those for the aforementioned preparation C were performed to prepare the 0.3 w/v % OFLX-TG (Comparative Preparation E) for comparison.

In the prepared Comparative Preparation E, the viscosity at 20° C. was 45.0 mPa·s, a gelation temperature was 28° C., and a temperature at which the viscosity of a preparation becomes 100 mPa·s or more was 34° C.

<Test to Examine the Penetration of Ofloxacin (OFLX) Thermo-setting Gel Ophthalmic Solution or TARIVID Ophthalmic Solution into the Surface of Conjunctiva, in Conjunctiva and in Aqueous Humor of Rabbit>

Each 50 μL of three formulations of OFLX thermo-setting gel ophthalmic solutions (Preparation C, Preparation D and Comparative Preparation E) prepared in Examples or TARIVID ophthalmic solution (manufactured by Santen Pharmaceutical Co., Ltd., containing 0.3% OFLX) was instilled to Japanese White rabbits (male, body weight: 2.0 to 2.6 kg), and the OFLX concentrations in conjunctiva, on the surface of conjunctiva and in aqueous humor at 15 minutes, and 1 and 2 hours after administration were determined.

The concentrations of OFLX in conjunctiva, on the surface of conjunctiva and in aqueous humor were obtained according to the same manner as that of Test Example 13.

The resulting OFLX concentrations in conjunctiva, on the surface of conjunctiva and in aqueous humor are shown in Tables 18, 19 and 20, respectively.

TABLE 18

Concentrations in conjunctiva after administration of ofloxacin (OFLX) thermo-setting gel ophthalmic solution or TARIVID ophthalmic solution to albino rabbits (μg/g, n = 4 to 6)

| Ophthalmic solution | | Hours after application | | |
|---|---|---|---|---|
| | | 15 min | 1 hr | 2 hr |
| Preparation C | Average | 55.06##*** | 5.66* | 0.76##*** |
| | ±SD | 11.03 | 4.10 | 0.17 |
| Preparation D | Average | 46.27#** | 3.07 | 0.74###** |
| | ±SD | 25.41 | 3.37 | 0.37 |
| Comparative Preparation E | Average | 17.22 | 3.89 | 0.19 |
| | ±SD | 5.68 | 2.84 | 0.10 |
| TARIVID ophthalmic solution | Average | 11.49 | 0.19 | 0.13 |
| | ±SD | 11.97 | 0.10 | 0.09 |

*$p < 0.05$,
**$p < 0.01$,
***$p < 0.001$ (vs TARIVID ophthalmic solution)
$p < 0.05$,
$p < 0.01$ (vs Comparative Preparation E) Tukey-kramer test From the results of Table 18, the concentrations of OFLX in conjunctiva at 15 minutes, and 1 and 2 hours after administration of Preparation C formulation showed significantly higher values at any time as compared with TARIVID ophthalmic solution, and showed significantly higher values at 15 minutes and 2 hours after administration as compared with Comparative Preparation E formulation. In addition, the concentrations of OFLX in conjunctiva at 15 minutes and 2 hours after administration of Preparation D formulation showed significantly higher values as compared with Comparative Preparation E formulation and TARIVID ophthalmic solution.

TABLE 19

Concentrations on the surface of conjunctiva after administration of ofloxacin (OFLX) thermo-setting gel ophthalmic solution or TARIVID ophthalmic solution to albino rabbits (μg/g, n = 4 to 6)

| Ophthalmic solution | | Hours after application | |
|---|---|---|---|
| | | 1 hr | 2 hr |
| Preparation C | Average | 3.75 | 0.30 |
| | ±SD | 4.53 | 0.11 |
| Preparation D | Average | 2.93 | 0.69 |
| | ±SD | 3.80 | 0.78 |
| Comparative Preparation E | Average | 1.89 | 0.33 |
| | ±SD | 1.83 | 0.26 |
| TARIVID ophthalmic solution | Average | 0.26 | 0.13 |
| | ±SD | 0.17 | 0.08 |

From the results of Table 19, the concentrations of OFLX on the surface of conjunctiva at 1 hour after administration of Preparation C and Preparation D formulations showed clearly higher values which are 14.4- and 11.3-fold the value of TARIVID ophthalmic solution, respectively. In addition, they showed clearly higher values which are 2.3- and 5.3-fold the values of TARIVID ophthalmic solution also at 2 hours after administration, respectively.

TABLE 20

Concentrations in aqueous humor after administration of ofloxacin (OFLX) thermo-setting gel ophthalmic solution or TARIVID ophthalmic solution to albino rabbits (μg/mL, n = 5 to 6)

| Ophthalmic solution | | 15 min | 1 hr | 2 hr |
|---|---|---|---|---|
| Preparation C | Average | 0.162 | 1.568* | 1.272* |
| | ±SD | 0.063 | 0.410 | 0.427 |
| Preparation D | Average | 0.167 | 1.534* | 1.335* |
| | ±SD | 0.044 | 0.423 | 0.860 |
| Comparative Preparation E | Average | 0.156 | 0.920 | 0.720 |
| | ±SD | 0.047 | 0.510 | 0.344 |
| TARIVID ophthalmic solution | Average | 0.200 | 0.706 | 0.440 |
| | ±SD | 0.088 | 0.160 | 0.078 |

*$p < 0.05$ (vs TARIVID ophthalmic solution) Tukey-kramer test

From the results of Table 20, the concentrations of OFLX in aqueous humor at 1 and 2 hours after administration of Preparation C and Preparation D formulations shows significantly higher values as compared with TARIVID ophthalmic solution.

From the above results, it was shown that, on the surface of conjunctiva, in conjunctiva and in aqueous humor, the higher concentration of OFLX remains over a long time of 2 or more hours when Preparation C or Preparation D formulations is administered than when a commercially available TARIVID ophthalmic solution is administered. From this, it was shown that Preparation C and Preparation D formulations have the far higher antibacterial effects as compared with TARIVID ophthalmic solution which is a commercially available ophthalmic solution. In addition, Preparation C and Preparation D formulations showed the higher ofloxacin concentrations on the surface of conjunctiva, in conjunctiva and in aqueous humor as compared with Comparative Preparation E formulation.

TEST EXAMPLE 15

[Test of Efficacy of Pharmaceutical Agent of LVFX-containing Thermally Gelling Preparation Using Rabbit Experimental *Pseudomonas aeruginosa* Keratitis Model]

<Preparation of LVFX-containing Thermally Gelling Preparation>

SM-4 (4.0 g) and Macrogol 4000 (4.0 g) were mixed, 70 mL of sterile purified water heated to 85° C. was added thereto, and the ingredients were dispersed by stirring. After confirmed that the ingredients were uniformly dispersed, the dispersion was cooled by ice while stirring. After confirmed that the whole became clear, 3.53 g of sodium citrate was gradually added, and dissolved with stirring. Furthermore, 0.5 g of levofloxacin (LVFX) was added, and dissolved with stirring. To this was added 1N NaOH to adjust to pH 7.8, and sterile purified water was added to a volume of 100 mL to obtain the 0.5 w/v % LVFX thermally gelling preparation (LVFX-TG) of the present invention.

In the prepared LVFX-TG, the viscosity at 20° C. was 19.6 mPa·s, a gelation temperature was 20° C., and a temperature at which the viscosity of a preparation became 100 mPa·s or more was 26° C.

<Test of Efficacy of Pharmaceutical Agent By Rabbit Experimental *Pseudomonas aeruginosa* Keratitis Model>

A test was performed with white house rabbits, 11 to 13 week old, and each test group consisted of 4 eyes. Test groups were as follows: a group of applying physiological saline to eyes 3 times a day, a group of applying CRAVIT (registered trademark) ophthalmic solution (manufactured by Santen Pharmaceutical Co., Ltd.) to eyes 3 times a day, a group of applying CRAVIT (registered trademark) ophthalmic solution (manufactured by Santen Pharmaceutical Co., Ltd.) to eyes once a day, and a group of applying LVFX-TG to eyes once a day.

The rabbit experimental *Pseudomonas aeruginosa* keratitis model was made according to the report by Hatano et al. (Japanese Review of Clinical Ophthalmology 79(7)(1985). 32-39).

A test was performed by applying 50 µL to eyes once a day or every 4 hours 3 times a day, starting from an inoculation day (0 day) for four consecutive days.

Observation of infectious symptom was performed 8, 22, 31, 46, 55, 70, 79 and 96 hours after bacterium inoculation according to the report by Kuriyama et al. (Folia ophthalmologica Japonica 44(4)(1993) 434-444). The infectious symptom was scored for each ocular tissue, and a sum of each score was obtained, which was used as an index for severity of infectious disease.

<Results>

The score of infectious symptom of each group is shown in FIG. 1.

In a physiological saline-administered group, there was a tendency that a score increased immediately after bacterium inoculation (infection was established), the infectious symptom became the severest 46 hours after bacterium inoculation and, thereafter, the symptom cured spontaneously although gradually.

In a commercially available LVFX ophthalmic solution-administered group, there was a tendency that the symptom did not become as severe after establishment of infection as a physiological saline-administered group, and cured gradually. In addition, the infectious symptom was slighter in a group administered 3 times a day than a group administered once a day.

In contrast to these groups, in the group administered LVFX-TG of the present invention, it was shown that the infectious symptom reduced rapidly after establishment of infection, and recovered to the state almost equivalent to that before bacterium inoculation after 96 hours. This shows that, in the group administered LVFX-TG of the present invention, the stronger efficacy of pharmaceutical agent is obtained in spite of once a day administration, as compared with a group of applying commercially available LVFX ophthalmic solution to eyes 3 times a day.

Thus, it is shown that, by using a thermally gelling preparation instead of a commercially available ophthalmic solution, decrease of the number of administration times (improvement in QOL) and the stronger effect can be obtained.

TEST EXAMPLE 16

[Test of Efficacy of Pharmaceutical Agent of OFLX-containing Thermally Gelling Preparation with Rabbit Experimental *Pseudomonas aeruginosa* Keratitis Model]

<Preparation of OFLX-containing Thermally Gelling Preparation>

SM-4 (4.0 g) and Macrogol 4000 (4.0 g) were mixed, 70 mL of sterile purified water heated to 85° C. was added thereto, and the ingredients were dispersed by stirring. After confirmed that the ingredients were uniformly dispersed, the dispersion was cooled by ice while stirring. After confirmed that the whole became clear, sodium citrate (3.53 g) was gradually added, and dissolved with stirring. Furthermore, 0.3 g of ofloxacin (OFLX) was added, and dissolved with stirring. To this was added 1N HCl to adjust to pH 6.5. And, sterile purified water was added to a total volume of 100 mL to obtain the 0.3 w/v % OFLX thermally gelling preparation (OFLX-TG) of the present invention.

In the prepared OFLX-TG, the viscosity at 20° C. was 19.7 mPa·s, a gelation temperature was 22° C., and a temperature at which the viscosity of a preparation became 100 mPa·s or more was 26° C.

<Test of Efficacy of Pharmaceutical Agent by Rabbit Experimental *Pseudomonas aeruginosa* Keratitis Model>

A test was performed as in Test Example 15. Test groups were as follows; a group of applying physiological saline to eyes 3 times a day, a group of applying CRAVIT (registered trademark) ophthalmic solution (manufactured by Santen Pharmaceutical Co., Ltd.) to eyes 3 times a day, and a group of applying OFLX-TG to eyes once a day.

A test was performed by applying 50 µL to eyes once a day or every 4 hours 3 times a day, starting from an inoculation day (0 day) for four consecutive days.

Observation of infectious symptom was performed 8, 22, 31, 46, 55, 70, 79 and 96 hours after bacterium inoculation according to the report by Kuriyama et al. (Folia ophthalmologica Japonica 44(4)(1993) 434-444). The infectious symptom was scored for each ocular tissue, and a sum of each score was obtained, which was used as an index for severity of infectious disease.

<Results>

Figure 2:
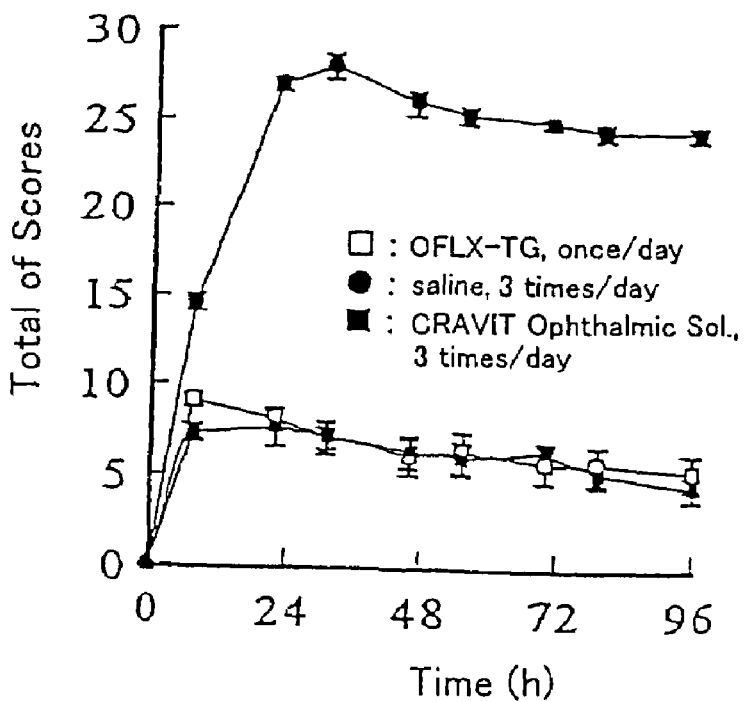
FIG. 2 is a graph showing the test results of Test Example 16 herein.

The score of infectious symptom of each group is shown in FIG. 2.

In a physiological saline-administered group, there was a tendency that a score increased immediately after bacterium inoculation (infection was established), the infectious symptom became the severest 32 hours after bacterium inoculation and, thereafter, the symptom cured spontaneously although gradually.

In a commercially available LVFX ophthalmic solution-administered group and the present OFLX-TG-administered group, there was a tendency that the symptom did not become as severe after establishment of infection as a physiological saline-administered group, and was cured little by little.

It is said that LVFX, which is an optically separated isomer of OFLX, has 2-fold stronger antibacterial activity than OFLX. In addition, the concentration of the preparation used in the present test is 0.3 w/v % OFLX in the case of OFLX-TG, while the concentration is 0.5 w/v % LVFX in the case of a commercially available LVFX ophthalmic solution.

The results of the present test show that a group of administration of a commercially available LVFX ophthalmic solution having the strong antibacterial activity and the high concentration 3 times a day, and a group of administration of OFLX-TG once a day have the approximately equivalent efficacy of pharmaceutical agent.

Thus, it is shown that, by using a thermally gelling preparation instead of a commercially available ophthalmic solution (OFLX is commercially available as TARIVID (registered trademark) ophthalmic solution), alleviation of the number of administration times (improvement in QOL) and the stronger effect can be obtained.

TEST EXAMPLE 17

[Test of Efficacy of Pharmaceutical Agent of OFLX-containing Thermally Gelling Preparation with Rabbit Experimental *Pseudomonas aeruginosa* Keratitis Serious Model]

<Test of Efficacy of Pharmaceutical Agent by Rabbit Experimental *Pseudomonas aeruginosa* Keratitis Model>

A test was performed with white house rabbits, 11 to 13 week old, and each test group consisted of 4 eyes. Test groups were as follows; a group of applying physiological saline to eyes 3 times a day, a group of applying CRAVIT (registered trademark) ophthalmic solution (manufactured by Santen Pharmaceutical Co., Ltd.) to eyes 3 times a day, and a group of applying OFLX-TG prepared in Test Example 16 to eyes once a day.

The rabbit experimental *Pseudomonas aeruginosa* keratitis model was made as in Test Example 15.

A test was performed by applying 50 µL to eyes once a day or every 4 hours 3 times a day starting from 24 hours after inoculation at a total of consecutive 4 days. The serious *Pseudomonas aeruginosa* infectious disease model was made by performing application to eyes not at 0 day after inoculation but 24 hours after inoculation.

Observation of infectious symptom was performed according to the same manner as that in Test Example 15, and 24, 32, 46, 55, 70, 79, 96, 103 and 120 hours after bacterium inoculation. The infectious symptom was scored for each ocular tissue, and a sum of each score was obtained, which was used as an index for severity of infectious disease.

<Results>

Figure 3:
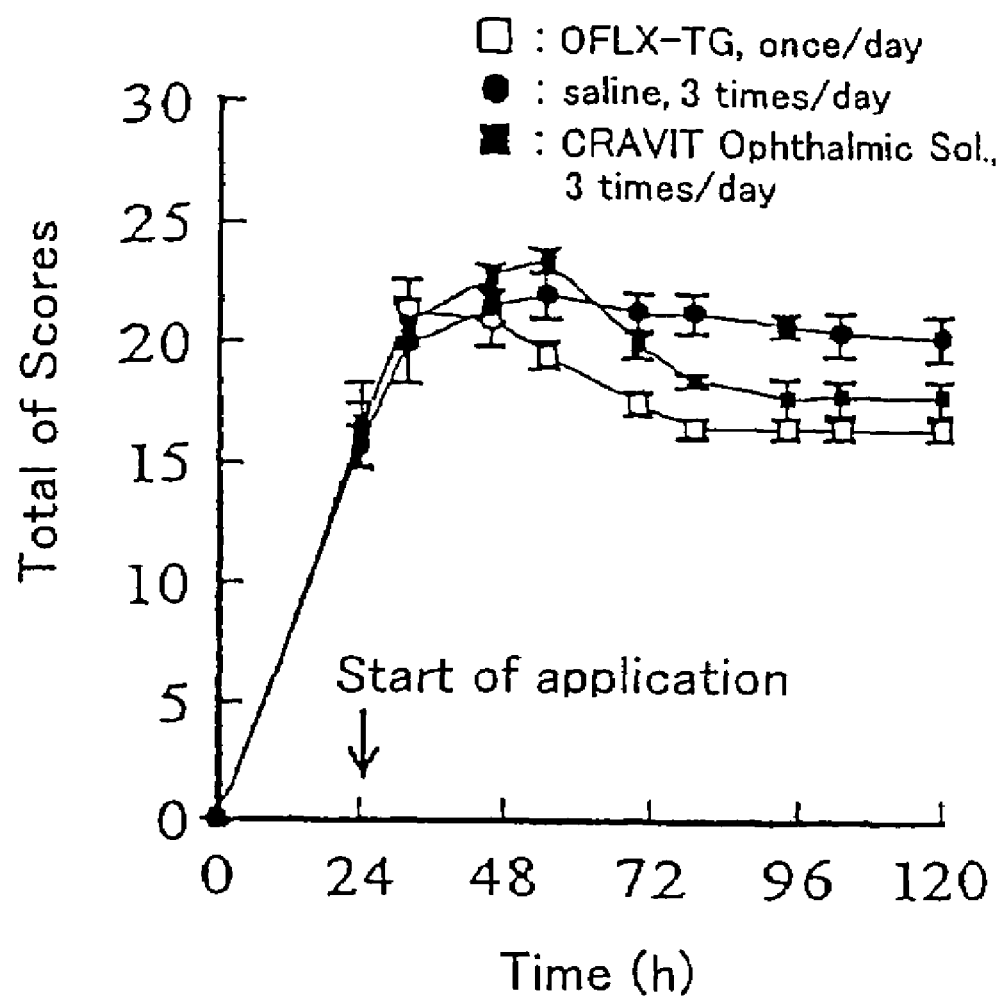
FIG. 3 is a graph showing the test results of Test Example 17 herein.

The score of infectious symptom of each group is shown in FIG. 3.

In a physiological saline-administered group, there was a tendency that a score increased immediately after bacterium inoculation (infection was established), the infectious symptom became the severest 55 hours after inoculation and, thereafter, the symptom cured spontaneously although extremely slightly.

In a commercially available LVFX ophthalmic solution-administered group, the infectious symptom became the severest 55 hours after inoculation like a physiological saline-administered group and showed almost the same progress as that of the physiological saline-administered group. However, after 55 hours, the symptom was rapidly reverted to restoration and the curing effect was shown as compared with the physiological saline-administered group.

On the other hand, in a group of administration of OFLX-TG of the present invention, the symptom became the severest at 32 hours after establishment of infection, but the score was equivalent to other administered groups at 32 hours. Thereafter, unlike other administered groups, it was made clear that the symptom did not become worse and was cured rapidly.

It is said that LVFX, which is an optically separated isomer of OFLX, has 2-fold stronger antibacterial activity than OFLX. In addition, the concentration of the preparation used in the present test is 0.3 w/v % OFLX in the case of OFLX-TG, while the concentration is 0.5 w/v % LVFX in the case of a commercially available LVFX ophthalmic solution.

The results of the present test show that a group of administration of OFLX-TG once a day is more excellent in the efficacy of pharmaceutical agent than a group of administration of a commercially available LVFX ophthalmic solution 3 times a day having the strong antibacterial activity and the high concentration.

Thus, it is shown that, by using a thermally gelling preparation instead of a commercially available ophthalmic solution (OFLX is commercially available as TARIVID (registered trademark) ophthalmic solution), decrease of the number of administration times (improvement in QOL) and the stronger effect can be obtained.

TEST EXAMPLE 18

[Pharmaceutical Agent Transference Test of Moxifloxacin Hydrochloride-containing Thermally Gelling Preparation into House Rabbit Eye Tissue]

<Preparing Procedure of a Preparation>

SM-4 (4.0 g) and Macrogol 4000 (4.0 g) were mixed, sterile purified water heated to 85° C. was added thereto, and the ingredients were dispersed by stirring. After confirmed that the ingredients were uniformly dispersed, the dispersion was ice-cooled while stirring. After confirmed that the whole became clear, sodium citrate (3.53 g) was gradually added, and dissolved with stirring. To this was added 0.32 g of moxifloxacin hydrochloride, and stirred until the ingredient is uniformly dissolved. Furthermore, 1N NaOH was added to adjust to pH 7.2, sterile purified water was added to a total volume of 100 mL to obtain moxifloxacin hydrochloride-containing thermally gelling preparation (hereinafter, MOLX-TG) of the present invention.

In the prepared MOLX-TG, the viscosity at 20° C. was 20.6 mPa·s, a gelation temperature was 22° C., and a temperature at which the viscosity of a preparation becomes 100 mPa·s or more was 26° C.

As a comparison, 0.32 g of moxifloxacin hydrochloride was dissolved in a physiological saline, pH was adjusted to 7.2 with 5N NaOH, and a physiological saline was added to a total volume of 100 mL to prepare a moxifloxacin hydrochloride-containing aqueous solution (hereinafter, comparative aqueous solution) for comparison.

<Test to Examine the Penetration of MOLX-TG or Comparative Aqueous Solution into the Surface of Conjunctive, in Conjunctiva and in Aqueous Humor of Rabbits>

Each 50 μL of the prepared MOLX thermo-setting gel preparation (MOLX-TG) formulation or MOLX aqueous ophthalmic solution (comparative aqueous solution) was instilled in Japanese White rabbits (male, body weight: 1.7 to 2.1 kg), and the MOLX concentrations in conjunctiva, on the surface of conjunctiva and in aqueous humor at 15 minutes, and 1 and 2 hours after administration were determined.

The concentrations of MOLX in conjunctiva, on the surface of conjunctiva and in aqueous humor were obtained as in Test Example 13.

The resulting MOLX concentrations in conjunctiva, on the surface of conjunctiva and in aqueous humor are shown in Tables 21, 22 and 23, respectively.

TABLE 21

Concentrations of MOLX in conjunctiva when 50 μL/eye of 0.3% moxifloxacin (MOLX) ophthalmic solution was instilled to albino rabbits (μg/g, n = 4 to 6).

| Ophthalmic solution | | Hours after application | | |
|---|---|---|---|---|
| | | 15 min | 1 hr | 2 hr |
| MOLX-TG | Average | 98.26*** | 8.45*** | 1.43** |
| | ±SD | 27.56 | 3.70 | 0.69 |
| Comparative aqueous solution | Average | 11.73 | 0.99 | 0.20 |
| | ±SD | 8.45 | 0.62 | 0.11 |

**$p < 0.01$,
***$p < 0.001$ (vs comparative aqueous solution) Aspin-Welch test

From the results of Table 21, the concentrations of MOLX in conjunctiva at 15 minutes, and 1 and 2 hours after application of MOLX-TG formulation showed significantly higher values at any time as compared with the comparative aqueous solution.

TABLE 22

Concentrations of MOLX on the surface of conjunctiva when 50 μL/eye of 0.3% moxifloxacin (MOLX) ophthalmic solution was instilled to albino rabbits (μg/g, n = 4 to 6)

| Ophthalmic solution | | Hours after application | | |
|---|---|---|---|---|
| | | 15 min | 1 hr | 2 hr |
| MOLX-TG | Average | 23.32** | 0.71* | 0.32* |
| | ±SD | 5.84 | 0.31 | 0.16 |
| Comparative aqueous solution | Average | 0.89 | 0.14 | 0.05 |
| | ±SD | 0.50 | 0.07 | 0.02 |

*$p < 0.05$,
**$p < 0.01$ (vs comparative aqueous solution) Aspin-Welch test

From the results of Table 22, the concentrations of MOLX on the surface of conjunctiva at 15 minutes, and 1 and 2 hours after application of MOLX-TG formulation showed significantly higher values at any time as compared with the comparative aqueous solution.

TABLE 23

Concentrations of MOLX in aqueous humor when 50 μL/eye of 0.3% moxifloxacin (MOLX) ophthalmic solution was instilled to albino rabbits (μg/mL, n = 5 to 6)

| Ophthalmic solution | | Hours after application | | |
|---|---|---|---|---|
| | | 15 min | 1 hr | 2 hr |
| MOLX-TG | Average | 2.126*** | 5.343** | 2.092** |
| | ±SD | 0.265 | 1.076 | 0.697 |
| Comparative aqueous solution | Average | 1.326 | 2.177 | 0.678 |
| | ±SD | 0.325 | 0.331 | 0.122 |

**$p < 0.01$,
***$p < 0.001$ (vs comparative aqueous solution) Student's t test or Aspin-Welch test From the results of Table 23, the concentrations of MOLX in aqueous humor at 15 minutes, and 1 and 2 hours after administration of MOLX-TG formulation showed significantly higher values at any time as compared with the comparative aqueous solution.

From the above results, it was shown that, on the surface of conjunctiva, in conjunctiva and in aqueous humor, the higher concentration of MOLX remains over a long time of 2 hours or longer when MOLX-TG formulation was administered than when the comparative aqueous solution was administered. From this, it was shown that MOLX-TG formulation has the far higher antibacterial effect as compared with the comparative aqueous solution.

TEST EXAMPLE 19

[Intraocular Pressure Reduction Effect of Isopropylunoproston-containing Thermally Gelling Preparation]

<Preparing Procedure of a Preparation>

SM-4 (2.3 g) and Macrogol 4000 (2.0 g) were mixed, 70 mL of sterile purified water heated to 85° C. was added thereto, and the ingredients were dispersed by stirring. After confirmed that the ingredients were dispersed, the dispersion was cooled by ice while stirring. After confirmed that the whole became clear, 3.53 g of sodium citrate was gradually added, and dissolved with stirring. To this was added 1N HCl to adjust to pH 6.5, and sterile purified water was added to a volume of 100 mL to prepare the thermally gelling base. Separately, 50 mL of Rescula (registered trademark) ophthalmic solution (manufactured by Uenoseiyaku) was freeze-dried. To this was added 50 mL of the aforementioned thermally gelling base, and the ingredients were dissolved with stirring under ice-cooling to prepare the isopropylunoproston-containing thermally gelling preparation.

In the prepared isopropylunoproston-containing thermally gelling preparation of the present invention, the viscosity at 20° C. was 6.3 mPa·s, a gelation temperature was 28° C., and a temperature at which the viscosity of a preparation became 100 mPa·s or more was 36° C.

<Intraocular Pressure Reduction Test Using White House Rabbit>

A test was performed using white house rabbits (body weight: 2.6 to 3.5 kg), and each test group consisted of 4 eyes. Test groups were as follows; a group of application of a physiological saline, a group of application of Rescula (registered trademark) ophthalmic solution which is a commercially available aqueous solution preparation, and a group of application of the isopropylunoproston-containing thermally gelling preparation of the present invention.

In the test, the ophthalmic solution was applied to left eye once and intraocular pressure at 6, 8, 10 and 12 hours after application were measured. Right eye remained untreated. An average intraocular pressure of a group of application of a physiological saline and an average intraocular pressure of a group of application of a commercially available aqueous solution or a group of application of the thermally gelling preparation of the present invention were compared respectively. Then, an intraocular pressure value of a group of application of a commercially available aqueous solution was subtracted from an intraocular pressure value of a group of application of a physiological saline, and this was regarded as a reduction of intraocular pressure due to application of a commercially available aqueous solution. Similarly, a reduction of intraocular pressure due to application of the thermally gelling preparation of the present invention was obtained. Furthermore, a ratio of a reduction of intraocular pressure due to application of the thermally gelling preparation of the present invention relative to a reduction of intraocular pressure due to application of a commercially available aqueous solution was obtained as an intraocular pressure reduction rate. The results are shown in Table 24.

TABLE 24

| | Intra ocular pressure reduction rate | | | |
|---|---|---|---|---|
| | 6 hours | 8 hours | 10 hours | 12 hours |
| Preparation of present invention | 1.4 | 2.2 | 1.5 | 1.6 |
| Commercially available aqueous ophthalmic solution | 1 | 1 | 1 | 1 |

It was shown that the thermally gelling preparation of the present invention has a higher intraocular pressure reduction rate as compared with a commercially available aqueous solution preparation even at 12 hours after application. This shows that the stronger efficacy of pharmaceutical agent can be continuously obtained by using the thermally gelling preparation of the present invention instead of a commercially available aqueous solution.

INDUSTRIAL APPLICABILITY

The present invention has the aforementioned constitution and, therefore, can provide an antibacterial aqueous pharmaceutical composition and an aqueous pharmaceutical composition which have a sufficiently low gelation temperature even when new quinolone antibacterial agents such as ofloxacin as the active ingredient and can be retained at the administration site for a long time by virtue of rapid viscosity increase after administration in spite of their being liquid at administration and thereby attain high availability of pharmaceutical agent. According to such the present invention, an antibacterial gelling ophthalmic solution having the high pharmaceutical agent concentration on the surface of conjunctiva, in conjunctiva and in aqueous humor can be provided. Furthermore, since the number of administration times of ophthalmic solution can be decreased according to the present invention, improvement in compliance is expected.

The invention claimed is:

1. An antibacterial aqueous pharmaceutical composition which comprises: 2.8 to 4 w/v % of methylcellulose, wherein 2 w/v % aqueous solution of said methylcellulose has a viscosity of 12 mPa·s or below at 20° C.;

1.5 to 2.3 w/v % of citric acid;

2 to 4 w/v % of polyethylene glycol; and 0.1 to 0.5 w/v % of ofloxacin.

2. An antibacterial aqueous pharmaceutical composition which comprises:

2.8 to 4 w/v % of methylcellulose, wherein a 2 w/v % aqueous solution of said methylcellulose has a viscosity of 12 mPa·s or below at 20° C.;

1.5 to 2.3 w/v % of citric acid;

2 to 4 w/v % of polyethylene glycol;

and 0.1 to 0.5 w/v % of at least one kind of new quinolone antibacterial agent selected from the group consisting of ofloxacin, levofloxacin and moxifloxacin hydrochloride.

3. An aqueous pharmaceutical composition which comprises:

2.3 to 8 w/v % of methylcellulose, wherein a 2 w/v % aqueous solution of said methylcellulose has a viscosity of 12 mPa·s or below at 20° C.;

0.14 to 4 w/v % of at least one kind of acid selected from the group consisting of multivalent carboxylic acid, lactic acid and gluconic acid; and an effective amount of a pharmaceutical agent, wherein said pharmaceutical agent is at least one member selected from the group consisting of ciprofloxacin hydrochloride, norfloxacin, lomefloxacin hydrochloride, gatifloxacin, carteolol hydrochloride, betaxolol hydrochloride, timolol maleate, pilocarpine hydrochloride, isopropylunoproston, nipradirol, bromfenac sodium, pranoprofen, diclofenac sodium, ketotifen fumarate, acitazanolast, disodium cromoglicate, tranilast, bethamethasone sodium phosphate, prednisolone acetate, fluorometolone, fluorescein sodium, gentamicin sulfate, prienoxine, cyclosporine A. acyclovir, tropicamide and phenylephrine hydrochloride.

4. An aqueous pharmaceutical composition which comprises:

2.3 to 8 w/v % of methylcellulose, wherein 2 w/v % aqueous solution of said methylcellulose has a viscosity of 12 mPa·s or below at 20° C.;

0.5 to 13 w/v % of polyethylene glycol; and an effective amount of a pharmaceutical agent, wherein said pharmaceutical agent is at least one member selected from the group consisting of ciprofloxacin hydrochloride, norfloxacin, lomefloxacin hydrochloride, gatifloxacin, carteolol hydrochloride, betaxolol hydrochloride, timolol maleate, pilocarpine hydrochloride, isopropylunoproston, nipradirol, bromfenac sodium, pranoprofen, diclofenac sodium, ketotifen fumarate, acitazanolast, disodium cromoglicate, tranilast, bethamethasone sodium phosphate, prednisolone acetate, fluorometolone, fluorescein sodium, gentamicin sulfate, prienoxine, cyclosporine A, acyclovir, tropicamide and phenylephrine hydrochloride.

5. An aqueous pharmaceutical composition which comprises:

2.3 to 8 w/v % of methylcellulose, wherein a 2 w/v % aqueous solution of said methylcellulose has a viscosity of 12 mPa·s or below at 20° C.;

0.14 to 4 w/v % of at least one kind of acid selected from the group consisting of multivalent carboxylic acid, lactic acid and gluconic acid;

0.5 to 13 w/v % of polyethylene glycol; and an effective amount of a pharmaceutical agent, wherein said pharmaceutical agent is at least one member selected from the group consisting of ciprofloxacin hydrochloride, norfloxacin, lomefloxacin hydrochloride, gatifloxacin, carteolol hydrochloride, betaxolol hydrochloride, timolol maleate, pilocarpine hydrochloride, isopropylunoproston, nipradirol, bromfenac sodium, pranoprofen, diclofenac sodium, ketotifen fumarate, acitazanolast, disodium cromoglicate, tranilast, bethametasone sodium, phosphate, prednisolone acetate, fluorometolone, fluorescein sodium, gentamicin sulfate, prienoxine, cyclosporine A, acyclovir, tropicamide and phenylephrine hydrochloride.

* * * * *

UNITED STATES PATENT AND TRADEMARK OFFICE
CERTIFICATE OF CORRECTION

PATENT NO. : 7,612,115 B2
APPLICATION NO. : 11/374450
DATED : November 3, 2009
INVENTOR(S) : Suzuki et al.

It is certified that error appears in the above-identified patent and that said Letters Patent is hereby corrected as shown below:

Claim 1, column 35, line 63, "2 w/v %" should read --a 2 w/v %--

Claim 3, column 36, line 31, "cyclosporine A. acyclovir" should read --cyclosporine A, acyclovir--

Claim 4, column 36, line 35, "2 w/v %" should read --a 2 w/v %--

Claim 5, column 37, line 3, "bethametasone sodium, phosphate,"
should read --bethametasone sodium phosphate,--

Signed and Sealed this

Second Day of February, 2010

David J. Kappos
*Director of the United States Patent and Trademark Office*

UNITED STATES PATENT AND TRADEMARK OFFICE
CERTIFICATE OF CORRECTION

PATENT NO.       : 7,612,115 B2
APPLICATION NO.  : 11/374450
DATED            : November 3, 2009
INVENTOR(S)      : Suzuki et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 208 days.

Signed and Sealed this

Nineteenth Day of October, 2010

David J. Kappos
*Director of the United States Patent and Trademark Office*